United States Patent
Mandai et al.

(10) Patent No.: US 11,421,171 B2
(45) Date of Patent: Aug. 23, 2022

(54) LUBRICATING BASE OIL FOR FLUID DYNAMIC BEARING

(71) Applicant: NEW JAPAN CHEMICAL CO., LTD., Kyoto (JP)

(72) Inventors: Yumi Mandai, Kyoto (JP); Hirotsugu Mochida, Kyoto (JP); Meguru Sugiyama, Kyoto (JP)

(73) Assignee: NEW JAPAN CHEMICAL CO., LTD., Kyoto (JP)

( * ) Notice: Subject to any disclaimer, the term of this patent is extended or adjusted under 35 U.S.C. 154(b) by 0 days.

(21) Appl. No.: 17/299,436

(22) PCT Filed: Dec. 17, 2019

(86) PCT No.: PCT/JP2019/049301
§ 371 (c)(1),
(2) Date: Jun. 3, 2021

(87) PCT Pub. No.: WO2020/129944
PCT Pub. Date: Jun. 25, 2020

(65) Prior Publication Data
US 2022/0056363 A1 Feb. 24, 2022

(30) Foreign Application Priority Data
Dec. 20, 2018 (JP) .............................. JP2018-237825

(51) Int. Cl.
*C10M 105/34* (2006.01)
*C07C 69/24* (2006.01)
(Continued)

(52) U.S. Cl.
CPC ........... *C10M 105/34* (2013.01); *C07C 69/24* (2013.01); *C10M 129/14* (2013.01);
(Continued)

(58) Field of Classification Search
CPC ............. C10M 105/34; C10M 129/10; C10M 169/04; C10M 133/12; C10M 2215/06;
(Continued)

(56) References Cited

U.S. PATENT DOCUMENTS 6,379,581 B1 * 4/2002 Kamakura ......... C10M 171/008
252/68
6,667,285 B1 * 12/2003 Kawahara ............ C10M 105/36
508/485

(Continued)

FOREIGN PATENT DOCUMENTS

JP 49-35308 A 4/1974
JP 4-357318 A 12/1992
(Continued)

OTHER PUBLICATIONS

International Search Report dated Mar. 17, 2020, issued in counterpart application No. PCT/JP2019/049301, w/English translation (6 pages).

(Continued)

*Primary Examiner* — Vishal V Vasisth
(74) *Attorney, Agent, or Firm* — WHDA, LLP

(57) ABSTRACT

An object of the present invention is to provide an ester-based lubricating base oil for a fluid bearing that has a high viscosity index and excellent evaporation resistance, hydrolytic stability, and low-temperature fluidity. The present invention relates to a lubricating base oil for a fluid bearing containing a compound represented by general formula (1):

(Continued)

wherein $R^1$ represents a linear $C_2$-$C_{16}$ alkyl group, m represents an integer of 2 to 10, and n represents an integer of 4 to 14.

6 Claims, 18 Drawing Sheets

(51) Int. Cl.

| | | |
|---|---|---|
| *C10M 129/14* | (2006.01) | |
| *C10M 133/12* | (2006.01) | |
| *C10M 141/06* | (2006.01) | |
| C10N 30/10 | (2006.01) | |
| C10N 40/02 | (2006.01) | |

(52) U.S. Cl.
CPC ........ *C10M 133/12* (2013.01); *C10M 141/06* (2013.01); *C10M 2207/024* (2013.01); *C10M 2207/2815* (2013.01); *C10M 2215/26* (2013.01); *C10N 2030/10* (2013.01); *C10N 2040/02* (2013.01)

(58) Field of Classification Search
CPC ...... C10M 2215/064; C10M 2207/023; C10M 2290/00; C10M 2207/026; C10M 2207/2825; C10M 2207/2815; C10N 2030/10; C10N 2040/02; C10N 2020/09; C10N 2020/02; C10N 2020/011; C10N 2020/071; C10N 2030/74; C10N 2070/00; C07C 67/60; C07C 69/24; C07C 67/08; C07C 29/34; F16C 33/103; F16C 17/02; F16C 33/104; F16C 33/109; F16C 33/102
See application file for complete search history.

(56) References Cited

U.S. PATENT DOCUMENTS

| | | |
|---|---|---|
| 2006/0019840 A1 | 1/2006 | Kawahara et al. |
| 2009/0182046 A1 | 7/2009 | Dierker et al. |
| 2009/0290821 A1 | 11/2009 | Hirata et al. |
| 2009/0318316 A1 | 12/2009 | Morishima |
| 2012/0218661 A1 | 8/2012 | Yoshida |
| 2014/0018270 A1 | 1/2014 | Kim et al. |
| 2014/0121286 A1 | 5/2014 | Dierker et al. |
| 2014/0121394 A1 | 5/2014 | Dierker et al. |
| 2016/0319215 A1 | 11/2016 | Hirooka et al. |
| 2020/0181519 A1 | 6/2020 | Takegami et al. |

FOREIGN PATENT DOCUMENTS

| | | |
|---|---|---|
| JP | 11-514778 A | 12/1999 |
| JP | 11-514779 A | 12/1999 |
| JP | 2000-500898 A | 1/2000 |
| JP | 2002-146374 A | 5/2002 |
| JP | 2003-119482 A | 4/2003 |
| JP | 2004-084839 A | 3/2004 |
| JP | 2005-290256 A | 10/2005 |
| JP | 2008-007741 A | 1/2008 |
| JP | 2008-069234 A | 3/2008 |
| JP | 2008-533070 A | 8/2008 |
| JP | 2009-203275 A | 9/2009 |
| JP | 2012-181888 A | 9/2012 |
| JP | 2014-019867 A | 2/2014 |
| JP | 2014-139306 A | 7/2014 |
| JP | 2014-227474 A | 12/2014 |
| JP | 2016-210843 A | 12/2016 |
| JP | 2017-031269 A | 2/2017 |
| JP | 2019-056080 A | 4/2019 |
| JP | 2019-085561 A | 6/2019 |
| WO | 9716829 A1 | 5/1997 |
| WO | 9718562 A1 | 5/1997 |
| WO | 2004018595 A1 | 3/2004 |
| WO | 2019/082865 A1 | 5/2019 |

OTHER PUBLICATIONS

Chao et al., "Esters from Branched-Chain Acids and Neopentylpolyols and Phenols as Base Fluids for Synthetic Lubricants", Industrial & Engineering Chemistry Product Research and Development, 1983, vol. 22(2), pp. 357-362 table II.

* cited by examiner

LUBRICATING BASE OIL FOR FLUID DYNAMIC BEARING

This application is a 371 of PCT/JP2019/049301 filed Dec. 17, 2019.

TECHNICAL FIELD

The present invention relates to a lubricating base oil for a fluid bearing.

BACKGROUND ART

Ball bearings and roller bearings have been used as bearings in motors mounted in, e.g., hard disk drives (HDDs). However, due to demand for, for example, downsizing, vibration reduction, and decreased motor noise, fluid bearings have been put into practical use.

Along with the higher performance of audiovisual equipment or office automation equipment, and the widespread use of cellular phones, spindle motors equipped with fluid bearings are being increasingly used. Due to the recent strong demand for higher speed and downsizing of spindle motors, fluid bearings are required to achieve lower torque. To meet the demand for lower torque, lubricating base oils with a relatively low viscosity have been selected. Examples of such low-viscosity lubricating base oils include synthetic hydrocarbon-based lubricating base oils such as poly-α-olefin; ester-based lubricating base oils such as aliphatic dibasic acid diester, neopentyl-type polyol ester, and fatty acid monoester; and the like. Lubricating base oils for fluid bearings that use such a base oil have been proposed (PTL 1 to 8).

Among these, ester-based lubricating base oils, which have excellent viscosity properties, low-temperature fluidity, etc., are often used as lubricating base oils for fluid bearings.

However, since such an ester-based lubricating base oil contains an ester group in its molecular structure, hydrolysis occurs due to moisture, which may be problematic when a spindle motor is used for a long period of time.

Additionally, sophistication of the heads and disks of HDDs has strongly required the prevention of contamination caused by outgassing (PTL 9). There have been development of a machine structure that prevents evaporation of the lubricating base oil and the modification of equipment so as to prevent the entry of generated outgas into the disk and head. The lubricating base oil for a fluid bearing has also been required to have improved evaporation resistance.

CITATION LIST

Patent Literature

PTL 1: JPH11-514778A
PTL 2: JPH11-514779A
PTL 3: JP2000-500898A
PTL 4: JP2003-119482A
PTL 5: WO2004/018595A
PTL 6: JP2004-084839A
PTL 7: JP2005-290256A
PTL 8: JP2008-007741A
PTL 9: JP2012-181888A

SUMMARY OF INVENTION

Technical Problem

An object of the present invention is to provide a lubricating base oil for a fluid bearing that has a high viscosity index and excellent evaporation resistance, hydrolytic stability, and low-temperature fluidity, and provide a compound suitable for this base oil.

Solution to Problem

The present inventors conducted extensive research to achieve the object, and found that a novel specific lubricating base oil for a fluid bearing containing 2-methyl aliphatic monocarboxylic acid ester has a high viscosity index and excellent evaporation resistance, hydrolytic stability, and low-temperature fluidity. The inventors then completed the present invention.

Specifically, the present invention provides the following compound, lubricating base oil for a fluid bearing containing the compound, etc.

Item 1.

A compound represented by general formula (1):

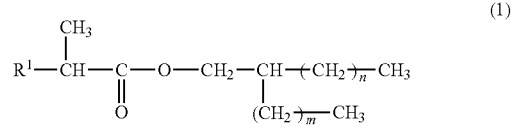

wherein $R^1$ represents a linear $C_2$-$C_{16}$ alkyl group, m represents an integer of 2 to 10, and n represents an integer of 4 to 14.

Item 2.

The compound according to Item 1, having 27 to 35 carbon atoms in total.

Item 3.

The compound according to Item 1 or 2, wherein the difference between n and m in general formula (1) is 2 to 9.

Item 4.

A lubricating base oil for a fluid bearing comprising the compound of any one of Items 1 to 3.

Item 5.

The lubricating base oil for a fluid bearing according to Item 4, wherein the content of the compound of any one of Items 1 to 3 is 90 mass % or more based on the total mass of the lubricating base oil for a fluid bearing.

Item 6.

A lubricating oil composition for a fluid bearing, the composition comprising the compound of any one of Items 1 to 3.

Item. 7

A lubricating oil composition for a fluid bearing, the composition comprising the lubricating base oil for a fluid bearing of Item 4 or 5.

Item 8.

The lubricating oil composition for a fluid bearing according to Item 6 or 7, further comprising an antioxidant.

Item 9.

The lubricating oil composition for a fluid bearing according to Item 8, wherein the antioxidant is a phenolic antioxidant and/or an amine-based antioxidant.

Item 10.

A fluid bearing comprising the lubricating oil composition for a fluid bearing of any one of Items 6 to 9.

Item 11.

A spindle motor comprising the fluid bearing of Item 10.

Advantageous Effects of Invention

The lubricating base oil for a fluid bearing according to the present invention has a high viscosity index and excellent evaporation resistance, hydrolytic stability, and low-temperature fluidity.

DESCRIPTION OF THE REFERENCE NUMERALS

Figure 1:
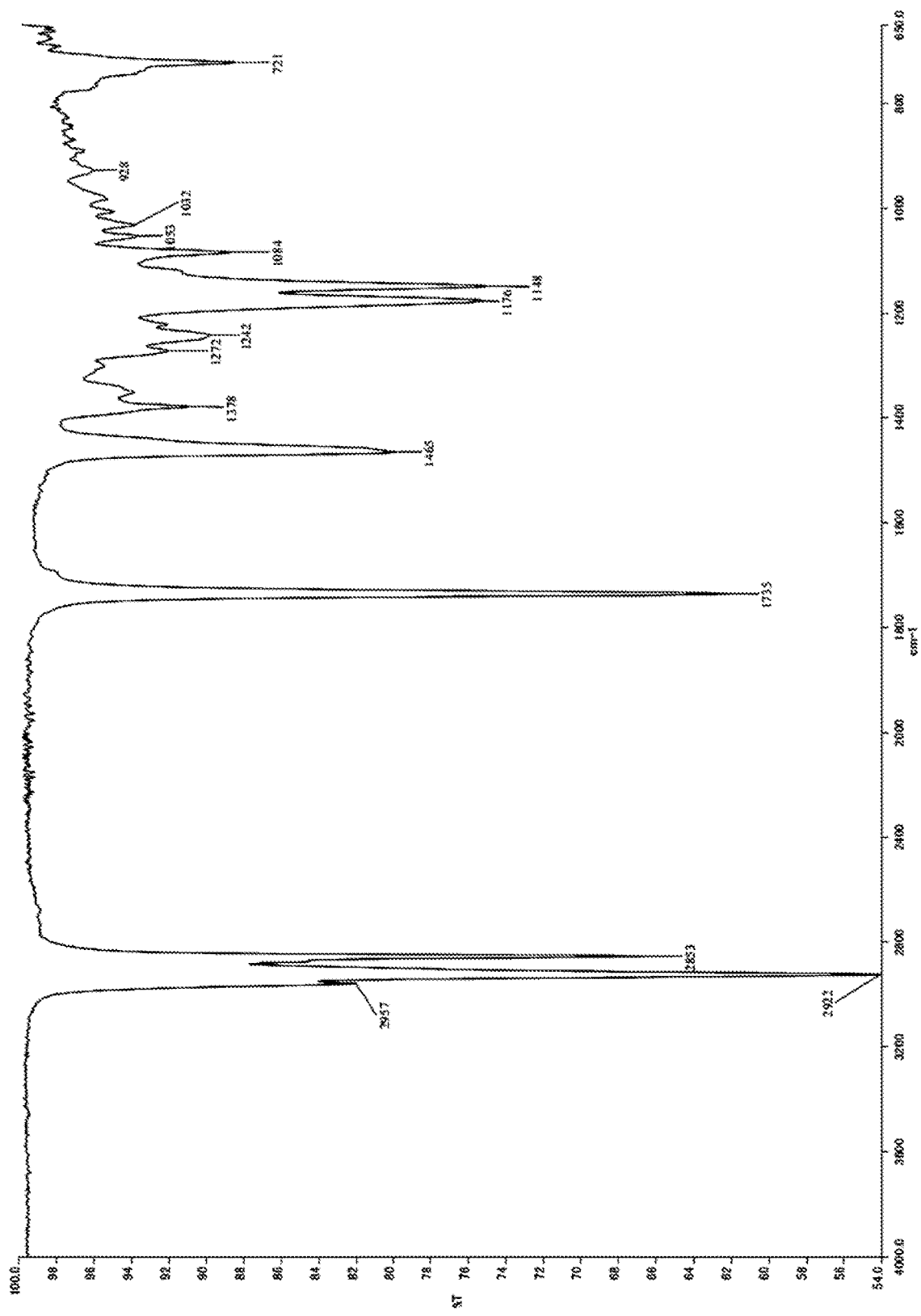
FIG. 1 illustrates an IR spectrum of 2-decyltetradecyl 2-methylpentanoate obtained in Example 1.

1 Shaft
2 Sleeve
3,4 Radial dynamic pressure-generating groove
5,6 Thrust dynamic pressure-generating groove
7 Thrust plate
8 Counter plate
9 Lubricating oil composition
10 Hub
11 Base
12 Stator coil
13 Rotor magnet

DESCRIPTION OF EMBODIMENTS

Lubricating Base Oil for a Fluid Bearing

The lubricating base oil for a fluid bearing of the present invention comprises a compound represented by the following general formula (1).

Compound Represented by General Formula (1)

The compound according to the present invention is 2-methyl aliphatic monocarboxylic acid ester represented by the following general formula (1)

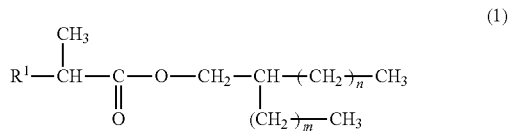

wherein $R^1$ represents a linear $C_2$-$C_{16}$ alkyl group, m represents an integer of 2 to 10, and n represents an integer of 4 to 14.

The compound represented by general formula (1) can be produced, for example, by subjecting to esterification a compound represented by general formula (1a) (2-methyl aliphatic monocarboxylic acid):

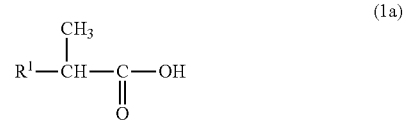

wherein $R^1$ is as defined above, and a compound represented by general formula (1b) (branched aliphatic alcohol):

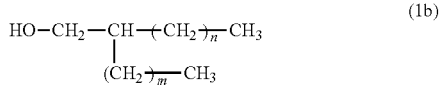

wherein m and n are as defined above.

In the compounds represented by general formula (1) or (1a), $R^1$ is a linear $C_2$-$C_{16}$ alkyl group, and particularly preferably a linear $C_2$-$C_{14}$ alkyl group. Specific examples of the compound represented by general formula (1a) include 2-methylbutanoic acid, 2-methylpentanoic acid, 2-methylhexanoic acid, 2-methylheptanoic acid, 2-methyloctanoic acid, 2-methylnonanoic acid, 2-methyldecanoic acid, 2-methylundecanoic acid, 2-methyldodecanoic acid, 2-methyltridecanoic acid, 2-methyltetradecanoic acid, 2-methylpentadecanoic acid, 2-methylhexadecanoic acid, 2-methylheptadecanoic acid, and 2-methyloctadecanoic acid.

In the compounds represented by general formula (1) or (1b), m represents an integer of 2 to 10, and n represents an integer of 4 to 14. The difference between n and m is preferably 2 to 9, and more preferably 2. The difference between n and m (n-m) is preferably 2 to 9, and more preferably 2. When the difference between n and m is 2, n is preferably an integer of 5 to 13, more preferably an integer of 6 to 12, and particularly preferably an integer of 7 to 11.

Specific examples of the compound represented by general formula (1b) include 2-propylheptanol, 2-propyloctanol, 2-propylnonanol, 2-propyldecanol, 2-propylundecanol, 2-propyldodecanol, 2-propyltridecanol, 2-propyltetradecanol, 2-propylpentadecanol, 2-propylhexadecanol, 2-propylheptadecanol, 2-butylheptanol, 2-butyloctanol, 2-butylnonanol, 2-butyldecanol, 2-butylundecanol, 2-butyldodecanol, 2-butyltridecanol, 2-butyltetradecanol, 2-butylpentadecanol, 2-butylhexadecanol, 2-butylheptadecanol, 2-pentylheptanol, 2-pentyloctanol, 2-pentylnonanol, 2-pentyldecanol, 2-pentylundecanol, 2-pentyldodecanol, 2-pentyltridecanol, 2-pentyltetradecanol, 2-pentylpentadecanol, 2-pentylhexadecanol, 2-pentylheptadecanol, 2-hexyloctanol, 2-hexylnonanol, 2-hexyldecanol, 2-hexylundecanol, 2-hexyldodecanol, 2-hexyltridecanol, 2-hexyltetradecanol, 2-hexylpentadecanol, 2-hexylhexadecanol, 2-hexylheptadecanol, 2-heptylnonanol, 2-heptyldecanol, 2-heptylundecanol, 2-heptyldodecanol, 2-heptyltridecanol, 2-heptyltetradecanol, 2-heptylpentadecanol, 2-heptylhexadecanol, 2-heptylheptadecanol, 2-octyldecanol, 2-octylundecanol, 2-octyldodecanol, 2-octyltridecanol, 2-octyltetradecanol, 2-octylpentadecanol, 2-octylhexadecanol, 2-octylheptadecanol, 2-nonylundecanol, 2-nonyldodecanol, 2-nonyltridecanol, 2-nonyltetradecanol, 2-nonylpentadecanol, 2-nonylhexadecanol, 2-nonylheptadecanol, 2-decyldodecanol, 2-decyltridecanol, 2-decyltetradecanol, 2-decylpentadecanol, 2-decylhexadecanol, 2-decylheptadecanol, 2-undecyltridecanol, 2-undecyltetradecanol, 2-undecylpentadecanol, 2-undecylhexadecanol, and 2-undecylheptadecanol.

The compound represented by general formula (1) preferably has 27 to 35 carbons in total, and particularly preferably 29 to 34 carbon atoms in total. 2-Methyl aliphatic monocarboxylic acid ester having less than 27 carbon atoms in total results in a lubricating base oil for a fluid bearing with poor evaporation resistance. 2-Methyl aliphatic monocarboxylic acid ester having more than 35 carbon atoms results in a lubricating base oil for a fluid bearing with high viscosity.

Specific examples of the compound represented by general formula (1) include 2-hexylhexadecyl 2-methylbutanoate, 2-octyltetradecyl 2-methylbutanoate, 2-nonyltridecyl 2-methylbutanoate, 2-decyldodecyl 2-methylbutanoate, 2-heptylhexadecyl 2-methylbutanoate, 2-nonyltetradecyl 2-methylbutanoate, 2-octylhexadecyl 2-methylbutanoate, 2-decyltetradecyl 2-methylbutanoate, 2-nonylhexadecyl 2-methylbutanoate, 2-undecyltetradecyl 2-methylbutanoate, 2-decylhexadecyl 2-methylbutanoate, 2-undecylpentadecyl 2-methylbutanoate, 2-decylheptadecyl 2-methylbutanoate, 2-undecylhexadecyl 2-methylbutanoate, 2-pentylhexadecyl 2-methylpentanoate, 2-heptyltetradecyl 2-methylpentanoate, 2-nonyldodecyl 2-methylpentanoate, 2-hexylhexadecyl 2-methylpentanoate, 2-octyltetradecyl 2-methylpentanoate, 2-nonyltridecyl 2-methylpentanoate, 2-decyldodecyl 2-methylpentanoate, 2-heptylhexadecyl 2-methylpentanoate, 2-nonyltetradecyl 2-methylpentanoate, 2-octylhexadecyl 2-methylpentanoate, 2-decyltetradecyl 2-methylpentanoate, 2-nonylhexadecyl 2-methylpentanoate, 2-undecyltetradecyl 2-methylpentanoate, 2-decylhexadecyl 2-methylpentanoate, 2-undecylpentadecyl 2-methylpentanoate, 2-decylheptadecyl 2-methylpentanoate, 2-undecylhexadecyl 2-methylpentanoate, 2-butylhexadecyl 2-methylhexanoate, 2-hexyltetradecyl 2-methylhexanoate, 2-octyldodecyl 2-methylhexanoate, 2-nonylundecyl 2-methylhexanoate, 2-pentylhexadecyl 2-methylhexanoate, 2-heptyltetradecyl 2-methylhexanoate, 2-nonyldodecyl 2-methylhexanoate, 2-hexylhexadecyl 2-methylhexanoate, 2-octyltetradecyl 2-methylhexanoate, 2-nonyltridecyl 2-methylhexanoate, 2-decyldodecyl 2-methylhexanoate, 2-heptylhexadecyl 2-methylhexanoate, 2-nonyltetradecyl 2-methylhexanoate, 2-octylhexadecyl 2-methylhexanoate, 2-decyltetradecyl 2-methylhexanoate, 2-nonylhexadecyl 2-methylhexanoate, 2-undecyltetradecyl 2-methylhexanoate, 2-decylhexadecyl 2-methylhexanoate, 2-undecylpentadecyl 2-methylhexanoate, 2-decylheptadecyl 2-methylhexanoate, 2-undecylhexadecyl 2-methylhexanoate, 2-propylhexadecyl 2-methylheptanoate, 2-pentyltetradecyl 2-methylheptanoate, 2-heptyldodecyl 2-methylheptanoate, 2-octylundecyl 2-methylheptanoate, 2-butylhexadecyl 2-methylheptanoate, 2-hexyltetradecyl 2-methylheptanoate, 2-octyldodecyl 2-methylheptanoate, 2-nonylundecyl 2-methylheptanoate, 2-pentylhexadecyl 2-methylheptanoate, 2-heptyltetradecyl 2-methylheptanoate, 2-nonyldodecyl 2-methylheptanoate, 2-hexylhexadecyl 2-methylheptanoate, 2-octyltetradecyl 2-methylheptanoate, 2-nonyltridecyl 2-methylheptanoate, 2-decyldodecyl 2-methylheptanoate, 2-heptylhexadecyl 2-methylheptanoate, 2-nonyltetradecyl 2-methylheptanoate, 2-octylhexadecyl 2-methylheptanoate, 2-decyltetradecyl 2-methylheptanoate, 2-nonylhexadecyl 2-methylheptanoate, 2-undecyltetradecyl 2-methylheptanoate, 2-decylhexadecyl 2-methylheptanoate, 2-undecylpentadecyl 2-methylheptanoate, 2-decylheptadecyl 2-methylheptanoate, 2-undecylhexadecyl 2-methylheptanoate, 2-butyltetradecyl 2-methyloctanoate, 2-hexyldodecyl 2-methyloctanoate, 2-heptylundecyl 2-methyloctanoate, 2-octyldecyl 2-methyloctanoate, 2-propylhexadecyl 2-methyloctanoate, 2-pentyltetradecyl 2-methyloctanoate, 2-heptyldodecyl 2-methyloctanoate, 2-octylundecyl 2-methyloctanoate, 2-butylhexadecyl 2-methyloctanoate, 2-hexyltetradecyl 2-methyloctanoate, 2-octyldodecyl 2-methyloctanoate, 2-nonylundecyl 2-methyloctanoate, 2-pentylhexadecyl 2-methyloctanoate, 2-heptyltetradecyl 2-methyloctanoate, 2-nonyldodecyl 2-methyloctanoate, 2-hexylhexadecyl 2-methyloctanoate, 2-octyltetradecyl 2-methyloctanoate, 2-nonyltridecyl 2-methyloctanoate, 2-decyldodecyl 2-methyloctanoate, 2-heptylhexadecyl 2-methyloctanoate, 2-nonyltetradecyl 2-methyloctanoate, 2-octylhexadecyl 2-methyloctanoate, 2-decyltetradecyl 2-methyloctanoate, 2-octylheptadecyl 2-methyloctanoate, 2-nonylhexadecyl 2-methyloctanoate, 2-undecyltetradecyl 2-methyloctanoate, 2-decylhexadecyl 2-methyloctanoate, 2-undecylpentadecyl 2-methyloctanoate, 2-propyltetradecyl 2-methylnonanoate, 2-pentyldodecyl 2-methylnonanoate, 2-hexylundecyl 2-methylnonanoate, 2-heptyldecyl 2-methylnonanoate, 2-butyltetradecyl 2-methylnonanoate, 2-hexyldodecyl 2-methylnonanoate, 2-heptylundecyl 2-methylnonanoate, 2-octyldecyl 2-methylnonanoate, 2-propylhexadecyl 2-methylnonanoate, 2-pentyltetradecyl 2-methylnonanoate, 2-heptyldodecyl 2-methylnonanoate, 2-octylundecyl 2-methylnonanoate, 2-butylhexadecyl 2-methylnonanoate, 2-hexyltetradecyl 2-methylnonanoate, 2-octyldodecyl 2-methylnonanoate, 2-nonylundecyl 2-methylnonanoate, 2-pentylhexadecyl 2-methylnonanoate, 2-heptyltetradecyl 2-methylnonanoate, 2-nonyldodecyl 2-methylnonanoate, 2-hexylhexadecyl 2-methylnonanoate, 2-octyltetradecyl 2-methylnonanoate, 2-nonyltridecyl 2-methylnonanoate, 2-decyldodecyl 2-methylnonanoate, 2-heptylhexadecyl 2-methylnonanoate, 2-nonyltetradecyl 2-methylnonanoate, 2-octylhexadecyl 2-methylnonanoate, 2-decyltetradecyl 2-methylnonanoate, 2-octylheptadecyl 2-methylnonanoate, 2-nonylhexadecyl 2-methylnonanoate, 2-undecyltetradecyl 2-methylnonanoate, 2-butyldodecyl 2-methyldecanoate, 2-pentylundecyl 2-methyldecanoate, 2-hexyldecyl 2-methyldecanoate, 2-heptylnonyl 2-methyldecanoate, 2-propyltetradecyl 2-methyldecanoate, 2-pentyldodecyl 2-methyldecanoate, 2-hexylundecyl 2-methyldecanoate, 2-heptyldecyl 2-methyldecanoate, 2-butyltetradecyl 2-methyldecanoate, 2-hexyldodecyl 2-methyldecanoate, 2-heptylundecyl 2-methyldecanoate, 2-octyldecyl 2-methyldecanoate, 2-propylhexadecyl 2-methyldecanoate, 2-pentyltetradecyl 2-methyldecanoate, 2-heptyldodecyl 2-methyldecanoate, 2-octylundecyl 2-methyldecanoate, 2-butylhexadecyl 2-methyldecanoate, 2-hexyltetradecyl 2-methyldecanoate, 2-octyldodecyl 2-methyldecanoate, 2-nonylundecyl 2-methyldecanoate, 2-pentylhexadecyl 2-methyldecanoate, 2-heptyltetradecyl 2-methyldecanoate, 2-nonyldodecyl 2-methyldecanoate, 2-hexylhexadecyl 2-methyldecanoate, 2-octyltetradecyl 2-methyldecanoate, 2-nonyltridecyl 2-methyldecanoate, 2-decyldodecyl 2-methyldecanoate, 2-hexylheptadecyl 2-methyldecanoate, 2-heptylhexadecyl 2-methyldecanoate, 2-nonyltetradecyl 2-methyldecanoate, 2-octylhexadecyl 2-methyldecanoate, 2-decyltetradecyl 2-methyldecanoate, 2-propyldodecyl 2-methylundecanoate, 2-butylundecyl 2-methylundecanoate, 2-pentyldecyl 2-methylundecanoate, 2-hexylnonyl 2-methylundecanoate, 2-butyldodecyl 2-methylundecanoate, 2-pentylundecyl 2-methylundecanoate, 2-hexyldecyl 2-methylundecanoate, 2-heptylnonyl 2-methylundecanoate, 2-propyltetradecyl 2-methylundecanoate, 2-pentyldodecyl 2-methylundecanoate, 2-hexylundecyl 2-methylundecanoate, 2-heptyldecyl 2-methylundecanoate, 2-butyltetradecyl 2-methylundecanoate, 2-hexyldodecyl 2-methylundecanoate, 2-heptylundecyl 2-methylundecanoate, 2-octyldecyl 2-methylundecanoate, 2-propylhexadecyl 2-methylundecanoate, 2-pentyltetradecyl 2-methylundecanoate, 2-heptyldodecyl 2-methylundecanoate, 2-octylundecyl 2-methylundecanoate, 2-butylhexadecyl 2-methylundecanoate, 2-hexyltetradecyl 2-methylundecanoate, 2-octyldodecyl 2-methylundecanoate, 2-nonylundecyl 2-methylundecanoate, 2-pentylhexadecyl 2-methylundecanoate, 2-heptyltetradecyl 2-methylundecanoate, 2-nonyldodecyl 2-methylundecanoate, 2-hexylhexadecyl 2-methylundecanoate, 2-octyltetradecyl 2-methylundecanoate, 2-nonyltridecyl 2-methylundecanoate, 2-decyldodecyl 2-methylundecanoate, 2-hexylheptadecyl 2-methylundecanoate, 2-heptylhexadecyl 2-methylundecanoate, 2-nonyltetradecyl 2-methylundecanoate, 2-propylundecyl 2-methyldodecanoate, 2-butyldecyl 2-methyldodecanoate, 2-pentylnonyl 2-methyldodecanoate, 2-hexyloctyl 2-methyldodecanoate, 2-propyldodecyl 2-methyldodecanoate, 2-butylundecyl 2-methyldodecanoate, 2-pentyldecyl 2-methyldodecanoate, 2-hexylnonyl 2-methyldodecanoate, 2-butyldodecyl 2-methyldodecanoate, 2-pentylundecyl 2-methyldodecanoate, 2-hexyldecyl 2-methyldodecanoate, 2-heptylnonyl 2-methyldodecanoate, 2-propyltetradecyl 2-methyldodecanoate, 2-pentyldodecyl 2-methyldodecanoate, 2-hexylundecyl 2-methyldodecanoate, 2-heptyldecyl 2-methyldodecanoate, 2-butyltetradecyl 2-methyldodecanoate, 2-hexyldodecyl 2-methyldodecanoate, 2-heptylundecyl 2-methyldodecanoate, 2-octyldecyl 2-methyldodecanoate, 2-propylhexadecyl 2-methyldodecanoate, 2-pentyltetradecyl 2-methyldodecanoate, 2-heptyldodecyl 2-methyldodecanoate, 2-octylundecyl 2-methyldodecanoate, 2-butylhexadecyl 2-methyldodecanoate, 2-hexyltetradecyl 2-methyldodecanoate, 2-octyldodecyl 2-methyldodecanoate, 2-nonylundecyl 2-methyldodecanoate, 2-pentylhexadecyl 2-methyldodecanoate, 2-heptyltetradecyl 2-methyldodecanoate, 2-nonyldodecyl 2-methyldodecanoate, 2-hexylhexadecyl 2-methyldodecanoate, 2-octyltetradecyl 2-methyldodecanoate, 2-nonyltridecyl 2-methyldodecanoate, 2-decyldodecyl 2-methyldodecanoate, 2-propyldecyl 2-methyltridecanoate, 2-butylnonyl 2-methyltridecanoate, 2-pentyloctyl 2-methyltridecanoate, 2-propylundecyl 2-methyltridecanoate, 2-butyldecyl 2-methyltridecanoate, 2-pentylnonyl 2-methyltridecanoate, 2-hexyloctyl 2-methyltridecanoate, 2-propyldodecyl 2-methyltridecanoate, 2-butylundecyl 2-methyltridecanoate, 2-pentyldecyl 2-methyltridecanoate, 2-hexylnonyl 2-methyltridecanoate, 2-butyldodecyl 2-methyltridecanoate, 2-pentylundecyl 2-methyltridecanoate, 2-hexyldecyl 2-methyltridecanoate, 2-heptylnonyl 2-methyltridecanoate, 2-propyltetradecyl 2-methyltridecanoate, 2-pentyldodecyl 2-methyltridecanoate, 2-hexylundecyl 2-methyltridecanoate, 2-heptyldecyl 2-methyltridecanoate, 2-butyltetradecyl 2-methyltridecanoate, 2-hexyldodecyl 2-methyltridecanoate, 2-heptylundecyl 2-methyltridecanoate, 2-octyldecyl 2-methyltridecanoate, 2-propylhexadecyl 2-methyltridecanoate, 2-pentyltetradecyl 2-methyltridecanoate, 2-heptyldodecyl 2-methyltridecanoate, 2-octylundecyl 2-methyltridecanoate, 2-butylhexadecyl 2-methyltridecanoate, 2-hexyltetradecyl 2-methyltridecanoate, 2-octyldodecyl 2-methyltridecanoate, 2-nonylundecyl 2-methyltridecanoate, 2-pentylhexadecyl 2-methyltridecanoate, 2-heptyltetradecyl 2-methyltridecanoate, 2-nonyldodecyl 2-methyltridecanoate, 2-propylnonyl 2-methyltetradecanoate, 2-butyloctyl 2-methyltetradecanoate, 2-pentylheptyl 2-methyltetradecanoate, 2-propyldecyl 2-methyltetradecanoate, 2-butylnonyl 2-methyltetradecanoate, 2-pentyloctyl 2-methyltetradecanoate, 2-propylundecyl 2-methyltetradecanoate, 2-butyldecyl 2-methyltetradecanoate, 2-pentylnonyl 2-methyltetradecanoate, 2-hexyloctyl 2-methyltetradecanoate, 2-propyldodecyl 2-methyltetradecanoate, 2-butylundecyl 2-methyltetradecanoate, 2-pentyldecyl 2-methyltetradecanoate, 2-hexylnonyl 2-methyltetradecanoate, 2-butyldodecyl 2-methyltetradecanoate, 2-pentylundecyl 2-methyltetradecanoate, 2-hexyldecyl 2-methyltetradecanoate, 2-heptylnonyl 2-methyltetradecanoate, 2-propyltetradecyl 2-methyltetradecanoate, 2-pentyldodecyl 2-methyltetradecanoate, 2-hexylundecyl 2-methyltetradecanoate, 2-heptyldecyl 2-methyltetradecanoate, 2-butyltetradecyl 2-methyltetradecanoate, 2-hexyldodecyl 2-methyltetradecanoate, 2-heptylundecyl 2-methyltetradecanoate, 2-octyldecyl 2-methyltetradecanoate, 2-propylhexadecyl 2-methyltetradecanoate, 2-pentyltetradecyl 2-methyltetradecanoate, 2-heptyldodecyl 2-methyltetradecanoate, 2-octylundecyl 2-methyltetradecanoate, 2-butylhexadecyl 2-methyltetradecanoate, 2-hexyltetradecyl 2-methyltetradecanoate, 2-octyldodecyl 2-methyltetradecanoate, 2-nonylundecyl 2-methyltetradecanoate, 2-butyloctyl 2-methylpentadecanoate, 2-pentylnonyl 2-methylpentadecanoate, 2-hexyldecyl 2-methylpentadecanoate, 2-heptylundecyl 2-methylpentadecanoate, 2-propylheptyl 2-methylhexadecanoate, 2-propyloctyl 2-methylhexadecanoate, 2-butylheptyl 2-methylhexadecanoate, 2-propylnonyl 2-methylhexadecanoate, 2-butyloctyl 2-methylhexadecanoate, 2-pentylheptyl 2-methylhexadecanoate, 2-propyldecyl 2-methylhexadecanoate, 2-butylnonyl 2-methylhexadecanoate, 2-pentyloctyl 2-methylhexadecanoate, 2-propylundecyl 2-methylhexadecanoate, 2-butyldecyl 2-methylhexadecanoate, 2-pentylnonyl 2-methylhexadecanoate, 2-hexyloctyl 2-methylhexadecanoate, 2-propyldodecyl 2-methylhexadecanoate, 2-butylundecyl 2-methylhexadecanoate, 2-pentyldecyl 2-methylhexadecanoate, 2-hexylnonyl 2-methylhexadecanoate, 2-butyldodecyl 2-methylhexadecanoate, 2-pentylundecyl 2-methylhexadecanoate, 2-hexyldecyl 2-methylhexadecanoate, 2-heptylnononyl 2-methylhexadecanoate, 2-propyltetradecyl 2-methylhexadecanoate, 2-pentyldodecyl 2-methylhexadecanoate, 2-hexylundecyl 2-methylhexadecanoate, 2-heptyldecyl 2-methylhexadecanoate, 2-butyltetradecyl 2-methylhexadecanoate, 2-hexyldodecyl 2-methylhexadecanoate, 2-heptylundecyl 2-methylhexadecanoate, 2-octyldecyl 2-methylhexadecanoate, 2-propylheptyl 2-methylheptadecanoate, 2-butyloctyl 2-methylheptadecanoate, 2-pentylnonyl 2-methylheptadecanoate, 2-hexyldecyl 2-methylheptadecanoate, 2-propylheptyl 2-methyloctadecanoate, 2-propyloctyl 2-methyloctadecanoate, 2-butylheptyl 2-methyloctadecanoate, 2-propylnonyl 2-methyloctadecanoate, 2-butyloctyl 2-methyloctadecanoate, 2-pentylheptyl 2-methyloctadecanoate, 2-propyldecyl 2-methyloctadecanoate, 2-butylnonyl 2-methyloctadecanoate, 2-pentyloctyl 2-methyloctadecanoate, 2-propylundecyl 2-methyloctadecanoate, 2-butyldecyl 2-methyloctadecanoate, 2-pentylnonyl 2-methyloctadecanoate, 2-hexyloctyl 2-methyloctadecanoate, 2-propyldodecyl 2-methyloctadecanoate, 2-butylundecyl 2-methyloctadecanoate, 2-pentyldecyl 2-methyloctadecanoate, 2-hexylnonyl 2-methyloctadecanoate, 2-butyldodecyl 2-methyloctadecanoate, 2-pentylundecyl 2-methyloctadecanoate, 2-hexyldecyl 2-methyloctadecanoate, and 2-heptylnonyl 2-methyloctadecanoate. In particular, the following are preferable: 2-decyltetradecyl 2-methylbutanoate, 2-nonyltridecyl 2-methylpentanoate, 2-decyltetradecyl 2-methylpentanoate, 2-octyldodecyl 2-methylhexanoate, 2-nonyltridecyl 2-methylhexanoate, 2-decyltetradecyl 2-methylhexanoate, 2-pentylhexadecyl 2-methylheptanoate, 2-heptyltetradecyl 2-methylheptanoate, 2-octyldodecyl 2-methylheptanoate, 2-nonyltridecyl 2-methylheptanoate, 2-decyltetradecyl 2-methylheptanoate, 2-heptylundecyl 2-methyloctanoate, 2-octyldodecyl 2-methyloctanoate, 2-nonyltridecyl 2-methyloctanoate, 2-decyltetradecyl 2-methyloctanoate, 2-heptylundecyl 2-methylnonanoate, 2-octyldodecyl 2-methylnonanoate, 2-nonyltridecyl 2-methylnonanoate, 2-decyltetradecyl 2-methylnonanoate, 2-heptylundecyl 2-methyldecanoate, 2-hexyldecyl 2-methyldecanoate, 2-octyldodecyl 2-methyldecanoate, 2-nonyltridecyl 2-methyldecanoate, 2-decyltetradecyl 2-methyldecanoate, 2-hexyldecyl 2-methylundecanoate, 2-heptylundecyl 2-methylundecanoate, 2-octyldodecyl 2-methylundecanoate, 2-nonyltridecyl 2-methylundecanoate, 2-pentylnonyl 2-methyldodecanoate, 2-hexyldecyl 2-methyldodecanoate, 2-heptylundecyl 2-methyldodecanoate, 2-octyldodecyl 2-methyldodecanoate, 2-nonyltridecyl 2-methyldodecanoate, 2-pentylnonyl 2-methyltridecanoate, 2-hexyldecyl 2-methyltridecanoate, 2-heptylundecyl 2-methyltridecanoate, 2-octyldodecyl 2-methyltridecanoate, 2-butyloctyl 2-methyltetradecanoate, 2-pentylnonyl 2-methyltetradecanoate, 2-hexyldecyl 2-methyltetradecanoate, 2-heptylundecyl 2-methyltetradecanoate, 2-octyldodecyl 2-methyltetradecanoate, 2-butyloctyl 2-methylpentadecanoate, 2-pentylnonyl 2-methylpentadecanoate, 2-hexyldecyl 2-methylpentadecanoate, 2-heptylundecyl 2-methylpentadecanoate, 2-butyloctyl 2-methylhexadecanoate, 2-pentylnonyl 2-methylhexadecanoate, 2-hexyldecyl 2-methylhexadecanoate, and 2-heptylundecyl 2-methylhexadecanoate.

The content of the compound represented by general formula (1) in the lubricating base oil for a fluid bearing is preferably 90 mass % or more, more preferably 95 mass % or more, and particularly preferably 98 mass % or more.

The lubricating base oil for a fluid bearing preferably has a kinematic viscosity at 40° C. of 8 mm$^2$/s or more and less than 17 mm$^2$/s, and more preferably 10 mm$^2$/s or more and less than 14 mm$^2$/s. When the kinematic viscosity at 40° C. is 8 mm$^2$/s or more, the rigidity of the fluid lubrication film becomes excellent. When the kinematic viscosity at 40° C. is less than 17 mm$^2$/s, the energy loss is small. The kinematic viscosity is a value obtained by the method described in the Examples below.

The lubricating base oil for a fluid bearing preferably has a viscosity index of 130 or more, and particularly preferably 140 or more. The higher the viscosity index, the better the viscosity-temperature characteristics. The viscosity index is a value obtained by the method described in the Examples below.

The evaporation resistance of the lubricating base oil for a fluid bearing can be evaluated, for example, by using as an index the temperature at which the mass is reduced by 5% as measured with a TG-DTA device. The temperature at which the mass of the lubricating base oil for a fluid bearing is reduced by 5% is preferably 250° C. or more, and particularly preferably 260° C. or more. The higher the temperature at which the mass is reduced by 5%, the better the evaporation resistance. The temperature at which the mass is reduced by 5% is a value obtained in the evaporation resistance test described in the Examples below.

The hydrolytic stability (hydrolysis resistance) of the lubricating base oil for a fluid bearing can be evaluated, for example, according to the amount of increase in the acid value after a hydrolysis test. The amount of increase in the acid value of the lubricating base oil for a fluid bearing after a hydrolysis test is preferably 0.5 mg KOH/g or less, and particularly preferably 0.15 mg KOH/g or less. The smaller the amount of increase in the acid value after a hydrolysis test, the better the hydrolytic stability. The amount of increase in the acid value after a hydrolysis test is a value obtained in the hydrolytic stability test described in the Examples below.

The low-temperature fluidity of the lubricating base oil for a fluid bearing can be evaluated, for example, according to the melting point. The lubricating base oil for a fluid bearing has a melting point of preferably 0° C. or below, and particularly preferably −10° C. or below. The lower the melting point, the better the low-temperature fluidity. The melting point is a value obtained by the method described in the Examples below.

Because of its excellent hydrolytic stability, excellent low-temperature fluidity, a high viscosity index, and excellent evaporation resistance, the lubricating base oil for a fluid bearing is suitably used as a lubricating base oil for a fluid bearing.

The lubricating base oil for a fluid bearing may contain a base oil (additional base oil) other than the compound represented by general formula (1). Examples of additional base oils include mineral oils (hydrocarbon oils obtained by purification of petroleum); poly-α-olefins; polybutenes; alkylbenzenes; alkylnaphthalenes; alicyclic hydrocarbon oils; isomerized oils of synthetic hydrocarbons obtained by the Fischer-Tropsch process and like synthetic hydrocarbon oils; animal and vegetable oils; organic acid esters other than the compound represented by general formula (1); polyalkylene glycols; and ether-based base oils, such as polyvinyl ethers, polyphenyl ethers, and alkylphenyl ethers. At least one of these additional base oils may suitably be used.

Examples of mineral oils include solvent-refined mineral oils, mineral oils treated by hydrogenation, and wax isomerized oils; and usable mineral oils are those having a kinematic viscosity in the range of generally 1 to 25 mm$^2$/s, and preferably 2 to 20 mm$^2$/s at 100° C.

Examples of poly-α-olefins include polymers or copolymers of α-olefins having 2 to 16 carbon atoms (for example, ethylene, propylene, 1-butene, 1-hexene, 1-octene, 1-decene, 1-dodecene, 1-tetradecene, 1-hexadecene), the polymers or copolymers having a kinematic viscosity of 1 to 25 mm$^2$/s at 100° C. and a viscosity index of 100 or more, and particularly preferably a kinematic viscosity of 1.5 to 20 mm$^2$/s at 100° C. and a viscosity index of 120 or more.

Examples of polybutenes include those obtained by polymerizing isobutylene, and those obtained by copolymerizing isobutylene with normal butylene; and those having a kinematic viscosity in the wide range of 2 to 40 mm$^2$/s at 100° C. are generally usable.

Examples of alkylbenzenes include benzenes substituted with one or more linear or branched $C_1$-$C_{40}$ alkyl groups, such as monoalkylbenzenes, dialkylbenzenes, trialkylbenzenes, and tetraalkylbenzenes that have a molecular weight of 200 to 450.

Examples of alkylnaphthalenes include naphthalenes substituted with one or more linear or branched $C_1$-$C_{30}$ alkyl groups, such as monoalkylnaphthalenes and dialkylnaphthalenes.

Examples of animal and vegetable oils include beef tallow, lard, palm oil, coconut oil, rapeseed oil, castor oil, sunflower oil, and the like.

Examples of organic acid esters include fatty acid monoesters (excluding the compound represented by general formula (1)), aliphatic dibasic acid diesters, polyol esters, and other esters.

Examples of fatty acid monoesters (excluding the compound represented by general formula (1)) include ester compounds of a $C_5$-$C_{22}$ aliphatic linear or branched monocarboxylic acid and a $C_3$-$C_{22}$ linear or branched saturated or unsaturated aliphatic alcohol.

Examples of aliphatic dibasic acid diesters include diesters of a $C_3$-$C_{22}$ linear or branched saturated or unsaturated aliphatic alcohol with an aliphatic dibasic acid such as oxalic acid, malonic acid, succinic acid, glutaric acid, adipic acid, pimelic acid, suberic acid, azelaic acid, sebacic acid, 1,9-nonamethylenedicarboxylic acid, 1,10-decamethylenedicarboxylic acid, or an anhydride thereof.

For polyol esters, it is possible to use full esters of a polyol that has a neopentyl structure or a polyol that has a non-neopentyl structure with a $C_3$-$C_{22}$ linear or branched saturated or unsaturated aliphatic monocarboxylic acid. Examples of polyols that have a neopentyl structure include neopentyl glycol, 2,2-diethylpropanediol, 2-butyl-2-ethylpropanediol, trimethylolethane, trimethylolpropane, pentaerythritol, ditrimethylolpropane, dipentaerythritol, and the like. Examples of polyols that have a non-neopentyl structure include 1,3-propanediol, 1,4-butanediol, 1,5-pentanediol, 1,6-hexanediol, 1,7-heptanediol, 1,8-octanediol, 1,9-nonanediol, 1,10-decanediol, 1,2-propanediol, 2-methyl-1,3-propanediol, 1,3-butanediol, 2-methyl-1,4-butanediol, 1,4-pentanediol, 2-methyl-1,5-pentanediol, 3-methyl-1,5-pentanediol, 1,5-hexanediol, 2-methyl-1,6-hexanediol, 3-methyl-1,6-hexanediol, 1,6-heptanediol, 2-methyl-1,7-heptanediol, 3-methyl-1,7-heptanediol, 4-methyl-1,7-heptanediol, 1,7-octanediol, 2-methyl-1,8-octanediol, 3-methyl-1,8-octanediol, 4-methyl-1,8-octanediol, 1,8-nonanediol, 2-methyl-1,9-nonanediol, 3-methyl-1,9-nonanediol, 4-methyl-1,9-nonanediol, 5-methyl-1,9-nonanediol, 2-ethyl-1,3-hexanediol, glycerol, polyglycerol, sorbitol, and the like.

Examples of other esters include ester compounds of a polymerized fatty acid such as dimer acid or hydrogenated dimer acid, or a hydroxy fatty acid such as a condensed castor oil fatty acid or a hydrogenated condensed castor oil fatty acid, with a $C_3$-$C_{22}$ linear or branched saturated or unsaturated aliphatic alcohol.

Examples of polyalkylene glycols include a polymer prepared from an alcohol and one or more $C_2$-$C_4$ linear or branched alkylene oxides by ring-opening polymerization. Examples of alkylene oxides include ethylene oxide, propylene oxide, and butylene oxide; it is possible to use polymers prepared from one of these, or copolymers prepared from a mixture of two or more of these. It is also possible to use such polyalkylene glycols wherein the one or more hydroxy groups at one or both ends are etherified or esterified. The kinematic viscosity of the polymer is 5 to 1,000 mm$^2$/s (40° C.), and preferably 5 to 500 mm$^2$/s (40° C.)

Polyvinyl ethers are, for example, compounds obtained by polymerizing a vinyl ether monomer. Examples of monomers include methyl vinyl ether, ethyl vinyl ether, isopropyl vinyl ether, n-butyl vinyl ether, isobutyl vinyl ether, sec-butyl vinyl ether, tert-butyl vinyl ether, n-pentyl vinyl ether, n-hexyl vinyl ether, 2-methoxyethyl vinyl ether, 2-ethoxyethyl vinyl ether, and the like. The kinematic viscosity of the polymer is 5 to 1,000 mm$^2$/s (40° C.), and preferably 5 to 500 mm$^2$/s (40° C.)

Examples of polyphenyl ethers include compounds having a structure wherein the meta positions of two or more aromatic rings are connected by one or more ether linkages or thioether linkages; specifically, for example, bis(m-phenoxyphenyl)ether, m-bis(m-phenoxyphenoxy)benzene, and thioether wherein one or more of its oxygen atoms are replaced by one or more sulfur atoms.

Examples of alkylphenyl ethers include compounds wherein a polyphenyl ether is substituted with one or more linear or branched $C_6$-$C_{18}$ alkyl groups; in particular, alkyldiphenyl ethers containing one or more alkyl groups are preferable.

The recommended content of the additional base oil in the lubricating base oil for a fluid bearing is 10 mass % or less; to improve the balance of the physical properties, the content of the additional base oil in the lubricating base oil for a fluid bearing is more preferably 5 mass % or less. The lubricating base oil for a fluid bearing is particularly preferably composed of only the compound represented by general formula (1).

Lubricating Oil Composition for Fluid Bearing

The lubricating oil composition for a fluid bearing according to the present invention contains the lubricating base oil for a fluid bearing described above. To improve the performance of the lubricating base oil for a fluid bearing, the composition may contain additives (e.g., an antioxidant) in addition to the lubricating base oil for a fluid bearing.

Examples of antioxidants include phenolic antioxidants, amine-based antioxidants, and sulfur-based antioxidants. Of these, phenolic antioxidants and amine-based antioxidants are recommended.

Phenolic antioxidants for use include various known antioxidants used in the art, without any particular limitation. Among these phenolic antioxidants, those containing preferably 6 to 100 carbon atoms in total, and more preferably 20 to 80 carbon atoms in total, are recommended.

Specific examples include 2,6-di-tert-butylphenol, 2,6-di-tert-butyl-p-cresol, 4,4'-methylenebis(2,6-di-tert-butylphenol), 4,4'-butylidenebis(3-methyl-6-tert-butylphenol), 2,2'-methylenebis(4-ethyl-6-tert-butylphenol), 2,2'-methylenebis(4-methyl-6-tert-butylphenol), 4,4'-isopropylidenebisphenol, 2,4-dimethyl-6-tert-butylphenol, tetrakis[methylene-3-(3,5-di-tert-butyl-4-hydroxyphenyl) propionate]methane, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 2,2'-dihydroxy-3,3'-di(α- methylcyclohexyl)-5,5'-dimethyl-diphenylmethane, 2,2-isobutylidenebis(4,6-dimethylphenol), 2,6-bis(2'-hydroxy-3'-tert-butyl-5'-methylbenzyl)-4-methylphenol, 1,1'-bis(4-hydroxyphenyl)cyclohexane, 2,5-di-tert-amylhydroquinone, 2,5-di-tert-butylhydroquinone, 1,4-dihydroxyanthraquinone, 3-tert-butyl-4-hydroxyanisole, 2-tert-butyl-4-hydroxyanisole, 2,4-dibenzoylresorcinol, 4-tert-butylcatechol, 2,6-di-tert-butyl-4-ethylphenol, 2-hydroxy-4-methoxybenzophenone, 2,4-dihydroxybenzophenone, 2,2'-dihydroxy-4-methoxybenzophenone, 2,4,5-trihydroxybenzophenone, α-tocopherol, bis[2-(2-hydroxy-5-methyl-3-tert-butylbenzyl)-4-methyl-6-tert-butylphenyl]terephthalate, triethyleneglycol bis[3-(3-tert-butyl-5-methyl-4-hydroxyphenyl)propionate], 1,6-hexanediol-bis[3-(3,5-di-tert-butyl-4-hydroxyphenyl)propionate], and the like. Among these, 2,6-di-tert-butylphenol, 2,6-di-tert-butyl-p-cresol, 4,4'-methylenebis(2,6-di-tert-butylphenol), 4,4'-butylidenebis(3-methyl-6-tert-butylphenol), 2,2'-methylenebis(4-ethyl-6-tert-butylphenol), 2,2'-methylenebis(4-methyl-6-tert-butylphenol), 4,4'-isopropylidenebisphenol, 2,4-dimethyl-6-tert-butylphenol, tetrakis[methylene-3-(3,5-di-tert-butyl-4-hydroxyphenyl)propionate]methane, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 2,6-di-tert-butyl-4-ethylphenol, bis[2-(2-hydroxy-5-methyl-3-tert-butylbenzyl)-4-methyl-6-tert-butylphenyl]terephthalate, triethyleneglycol bis[3-(3-tert-butyl-5-methyl-4-hydroxyphenyl)propionate], and 1,6-hexanediol-bis[3-(3,5-di-tert-butyl-4-hydroxyphenyl)propionate] are particularly preferable. 2,6-di-tert-butyl-p-cresol, 4,4'-methylenebis(2,6-di-tert-butylphenol), and 2,6-di-tert-butyl-4-ethylphenol are most preferable.

These phenolic antioxidants may be used singly, or in a combination of two or more. The amount of phenolic antioxidant is typically 0.01 to 5 parts by mass, and preferably 0.1 to 2 parts by mass, per 100 parts by mass of the lubricating base oil for a fluid bearing.

As amine-based antioxidants, various known antioxidants used in the art can be used without any particular limitation. Among these amine-based antioxidants, those containing preferably 6 to 60 carbon atoms in total, and more preferably 20 to 40 carbon atoms in total, are preferable.

Specific examples include diphenylamines such as diphenylamine, monobutyldiphenylamine, monopentyldiphenylamine, monohexyl diphenylamine, monoheptyldiphenylamine, monooctyldiphenylamine, and like monoalkyldiphenylamines, in particular, mono($C_4$-$C_9$ alkyl) diphenylamines (i.e., diphenylamines wherein one of the two benzene rings is mono-substituted with an alkyl group, in particular, a $C_4$-$C_9$ alkyl group, i.e., monoalkyl-substituted diphenylamines), p,p'-dibutyldiphenylamine, p,p'-dipentyldiphenylamine, p,p'-dihexyldiphenylamine, p,p'-diheptyldiphenylamine, p,p'-dioctyldiphenylamine, p,p'-dinonyldiphenylamine, and like di(alkylphenyl)amines, in particular, p,p'-di($C_4$-$C_9$ alkylphenyl)amines (i.e., dialkyl-substituted diphenylamines wherein each of the two benzene rings is mono-substituted with an alkyl group, in particular, a $C_4$-$C_9$ alkyl group, and the two alkyl groups are identical), di(mono $C_4$-$C_9$ alkylphenyl)amines wherein the alkyl group on one of the benzene rings is different from the alkyl group on the other of the benzene rings, di(di-$C_4$-$C_9$ alkylphenyl) amines wherein at least one of the four alkyl groups on the two benzene rings is different from the rest of the alkyl groups; naphthylamines such as N-phenyl-1-naphthylamine, N-phenyl-2-naphthylamine, 4-octylphenyl-1-naphthylamine, and 4-octylphenyl-2-naphthylamine; phenylenediamines such as p-phenylenediamine, N-phenyl-N'-isopropyl-p-phenylenediamine, and N-phenyl-N'-(1,3-dimethylbutyl)-p-phenylenediamine; and the like. Among these, p,p'-dioctyldiphenylamine, p,p'-dinonyldiphenylamine, and N-phenyl-1-naphthylamine are particularly preferable.

In the present specification and claims, examples of alkyl include linear or branched $C_1$-$C_{20}$ alkyl, and preferable examples of alkyl include linear or branched $C_1$-$C_{12}$ alkyl. When there are a plurality of alkyl groups in the same molecule, the alkyl groups may be the same or different. When there are a plurality of alkyl groups having the same number of carbon atoms in the same molecule, the alkyl groups may be linear or branched.

The amine-based antioxidants may be used singly, or in a combination of two or more. The amount of the amine-based antioxidant is generally 0.01 to 5 parts by mass, and preferably 0.1 to 2 parts by mass, per 100 parts by mass of the lubricating base oil for a fluid bearing.

When one or more phenolic antioxidants and one or more amine-based antioxidants are used in combination, the amount of the combination to be added is typically 0.01 to 5 parts by mass, and preferably 0.1 to 2 parts by mass, per 100 parts by mass of the lubricating base oil for a fluid bearing. The ratio of the phenolic antioxidant to the amine-based antioxidant (mass ratio) can be suitably selected from a wide range without any particular limitation. Preferably, the recommended mass ratio of the phenolic antioxidant (I) to the amine-based antioxidant (II) ((I):(II)) is 1:0.05 to 20, and more preferably 1:0.2 to 5.

Examples of preferable combinations of a phenolic antioxidant and an amine-based antioxidant include a combination of one or more members selected from the group consisting of 2,6-di-tert-butyl-p-cresol, 4,4'-methylenebis(2, 6-di-tert-butylphenol), and 2,6-di-tert-butyl-4-ethylphenol, with one or more members selected from the group consisting of p,p'-dioctyldiphenylamine, p,p'-dinonyldiphenylamine, and N-phenyl-1-naphthylamine.

Specific examples of preferable combinations include a combination of 2,6-di-tert-butyl-p-cresol and p,p'-dioctyldiphenylamine, a combination of 2,6-di-tert-butyl-p-cresol and p,p'-dinonyldiphenylamine, a combination of 2,6-di-tert-butyl-p-cresol and N-phenyl-1-naphthylamine, a combination of 4,4'-methylenebis(2,6-di-tert-butylphenol) and p,p'-dioctyldiphenylamine, a combination of 4,4'-methylenebis(2,6-di-tert-butylphenol) and p,p'-dinonyldiphenylamine, a combination of 4,4'-methylenebis(2,6-di-tert-butylphenol) and N-phenyl-1-naphthylamine, a combination of 2,6-di-tert-butyl-4-ethylphenol and p,p'-dioctyldiphenylamine, a combination of 2,6-di-tert-butyl-4-ethylphenol and p,p'-dinonyldiphenylamine, a combination of 2,6-di-tert-butyl-4-ethylphenol and N-phenyl-1-naphthylamine, and the like. Among these, for example, a combination of 4,4'-methylenebis(2,6-di-tert-butylphenol) and p,p'-dioctyldiphenylamine, a combination of 4,4'-methylenebis(2,6-di-tert-butylphenol) and p,p'-dinonyldiphenylamine, and a combination of 4,4'-methylenebis(2,6-di-tert-butylphenol) and N-phenyl-1-naphthylamine are recommended as more effective combinations in terms of excellent heat resistance.

Incorporating an antioxidant as described above into the lubricating base oil for a fluid bearing suppresses, for example, decomposition of the lubricating base oil for a fluid bearing in the presence of air, thus improving the heat resistance of the lubricating oil composition for a fluid bearing.

In order to further improve the performance of the lubricating oil composition for a fluid bearing, the lubricating oil composition for a fluid bearing may suitably contain at least one additive selected from the group consisting of metal detergents, ashless dispersants, oiliness agents, antiwear agents, extreme-pressure agents, metal deactivators, rust inhibitors, viscosity index improvers, pour point depressants, hydrolysis inhibitors, and the like. The amounts of such additives are not particularly limited as long as the effect of the present invention is ensured, and specific examples are as described below.

Examples of usable metal detergents include Ca-petroleum sulfonate, overbased Ca-petroleum sulfonate, Ca-alkylbenzene sulfonate, overbased Ca-alkylbenzene sulfonate, Ba-alkylbenzene sulfonate, overbased Ba-alkylbenzene sulfonate, Mg-alkylbenzene sulfonate, overbased Mg-alkylbenzene sulfonate, Na-alkylbenzene sulfonate, overbased Na-alkylbenzene sulfonate, Ca-alkylnaphthalene sulfonate, overbased Ca-alkylnaphthalene sulfonate, and like metal sulfonates; Ca-phenate, overbased Ca-phenate, Ba-phenate, overbased Ba-phenate, and like metal phenates; Ca-salicylate, overbased Ca-salicylate and like metal salicylates; Ca-phosphonate, overbased Ca-phosphonate, Ba-phosphonate, overbased Ba-phosphonate, and like metal phosphonates; overbased Ca-carboxylates; and the like. When such a metal detergent is used, the amount may be generally 1 to 10 parts by mass, and preferably 2 to 7 parts by mass, per 100 parts by mass of the lubricating base oil for a fluid bearing.

Examples of ashless dispersants include polyalkenyl succinimides, polyalkenyl succinamides, polyalkenyl benzylamines, polyalkenyl succinic acid esters, and the like. These ashless dispersants may be used singly, or in combination. When such an ashless dispersant is used, the amount may be generally 1 to 10 parts by mass, and preferably 2 to 7 parts by mass, per 100 parts by mass of the lubricating base oil for a fluid bearing.

Examples of oiliness agents include stearic acid, oleic acid, and like saturated or unsaturated aliphatic monocarboxylic acids; dimer acid, hydrogenated dimer acid, and like polymerized fatty acids; ricinoleic acid, 12-hydroxystearic acid, and like hydroxyfatty acids; lauryl alcohol, oleyl alcohol, and like saturated or unsaturated aliphatic monoalcohols; stearyl amine, oleyl amine, and like saturated or unsaturated aliphatic monoamines; lauramide, oleamide, and like saturated or unsaturated aliphatic monocarboxylic acid amides; batyl alcohol, chimyl alcohol, selachyl alcohol, and like glycerin ethers; lauryl polyglycerol ether, oleyl polyglyceryl ether, and like alkyl or alkenyl polyglyceryl ethers; di(2-ethylhexyl)monoethanolamine, diisotridecyl monoethanolamine, and like poly(alkylene oxide) adducts of alkyl or alkenylamine; and the like. These oiliness agents may be used singly, or in combination. When such an oiliness agent is used, the amount may be generally 0.01 to 5 parts by mass, and preferably 0.1 to 3 parts by mass, per 100 parts by mass of the lubricating base oil for a fluid bearing.

Examples of antiwear agents and/or extreme-pressure agents include phosphorus-based compounds such as tricresyl phosphate, cresyldiphenyl phosphate, alkylphenyl phosphates, tributyl phosphate, dibutyl phosphate, and like phosphoric acid esters, tributyl phosphite, dibutyl phosphite, triisopropyl phosphite and like phosphorous acid esters, as well as amine salts thereof; sulfur-based compounds such as sulfurized oils and fats, sulfurized oleic acid and like sulfurized fatty acids, di-benzyl disulfide, sulfurized olefins, and dialkyl disulfides; organometallic compounds such as Zn-dialkyldithio phosphates, Mo-dialkyldithio phosphates, and Mo-dialkyldithio carbamates; and the like. These antiwear agents may be used singly, or in combination. When such an antiwear agent is used, the amount may be generally 0.01 to 10 parts by mass, and preferably 0.1 to 5 parts by mass, per 100 parts by mass of the lubricating base oil for a fluid bearing.

Examples of metal deactivators include benzotriazole-based compounds, thiadiazole-based compounds, gallic acid ester-based compounds, and the like. These metal deactivators may be used singly, or in combination. When such a metal deactivator is used, the amount may be generally 0.01 to 0.4 parts by mass, and preferably 0.01 to 0.2 parts by mass, per 100 parts by mass of the lubricating base oil for a fluid bearing.

Examples of rust inhibitors include dodecenylsuccinic acid half-esters, octadecenylsuccinic anhydride, dodecenylsuccinic amide, and like alkyl or alkenyl succinic acid derivatives; sorbitan monooleate, glycerol monooleate, pentaerythritol monooleate, and like partial esters of polyhydric alcohols; Ca-petroleum sulfonate, Ca-alkylbenzene sulfonate, Ba-alkylbenzene sulfonate, Mg-alkylbenzene sulfonate, Na-alkylbenzene sulfonate, Zn-alkylbenzene sulfonate, Ca-alkylnaphthalene sulfonate, and like metal sulfonates; rosin amine, N-oleyl sarcosine, and like amines; dialkyl phosphite amine salts; and the like. These rust inhibitors may be used singly, or in combination. When such a rust inhibitor is used, the amount may be generally 0.01 to 5 parts by mass, and preferably 0.05 to 2 parts by mass, per 100 parts by mass of the lubricating base oil for a fluid bearing.

Examples of viscosity index improvers include polyalkylmethacrylates, polyalkylstyrenes, polybutenes, ethylene-propylene copolymers, styrene-diene copolymers, styrene-maleic anhydride ester copolymers, and like olefin copolymers. These viscosity index improvers may be used singly or in combination. When such a viscosity index improver is used, the amount may be generally 0.1 to 15 parts by mass, preferably 0.5 to 7 parts by mass, per 100 parts by mass of the lubricating base oil for a fluid bearing.

Examples of pour point depressants include condensates of chlorinated paraffin and alkylnaphthalene; condensates of chlorinated paraffin and phenol; and polyalkylmethacrylates, polyalkylstyrenes, polybutenes, etc., which are also viscosity index improvers as mentioned above. These pour point depressants may be used singly or in combination. When such a pour point depressant is used, the amount may be generally 0.01 to 5 parts by mass, and preferably 0.1 to 3 parts by mass, per 100 parts by mass of the lubricating base oil for a fluid bearing.

Examples of usable hydrolysis inhibitors include alkyl glycidyl ethers, alkyl glycidyl esters, alkylene glycol glycidyl ethers, alicyclic epoxides, phenyl glycidyl ether and like epoxy compounds; and di-tert-butylcarbodiimide, 1,3-di-p-tolylcarbodiimide, and like carbodiimide compounds. The amount may be generally 0.05 to 2 mass, per 100 parts by mass of the lubricating base oil for a fluid bearing.

Fluid Bearing

Figure 18:
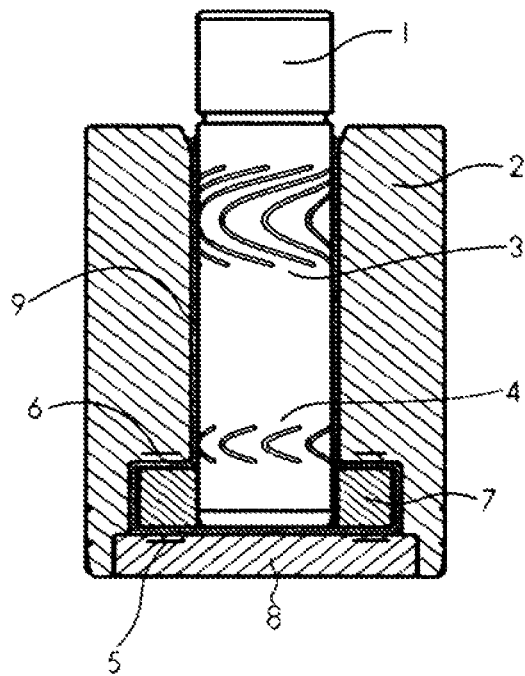
FIG. 18 illustrates an example of the cross-sectional surface of the fluid bearing according to the present invention.

The present invention also can provide a fluid bearing comprising the lubricating oil composition for a fluid bearing described above. Specific examples of the fluid bearing of the present invention include the fluid bearing shown in FIG. 18. FIG. 18 is an example of a cross-sectional view schematically showing an outline configuration of the fluid bearing of the present invention.

The fluid bearing of the present invention does not have a mechanism such as a ball bearing, and includes a shaft and a sleeve. The spacing between the shaft and the sleeve is maintained by a lubricating oil composition accommodated between them so that the shaft and the sleeve do not come into direct contact with each other. There is no particular mechanical limitation on the bearing as long as it is such a bearing. The fluid bearing shown in FIG. 1 is an example of a fluid bearing in which a shaft (1) is provided with radial dynamic pressure-generating grooves (3) and (4), and thrust dynamic pressure-generating grooves (5) and (6) are provided above and below a thrust plate (7). In this example, these dynamic pressure grooves (3), (4), (5), and (6) are formed in a herringbone shape; however, the shape of the dynamic pressure grooves (3), (4), (5), and (6) is not limited to these. The dynamic pressure grooves (3), (4), (5), and (6) may be formed in the shape of, for example, a spiral, an arc, or a straight line.

The radial dynamic pressure-generating grooves (3) and (4) may be formed on the inner peripheral surface of a sleeve (2) instead of the outer peripheral surface of the shaft (1). The thrust dynamic pressure-generating grooves (5) and (6) may be formed on the upper surface and the lower surface of the thrust plate (7) instead of the lower end surface of the sleeve (2) and the upper surface of a counter plate (8). The lubricating oil composition (9) of the present invention is enclosed in minute gaps between these dynamic pressure grooves (3), (4), (5), and (6), and their opposing surfaces.

In the fluid bearing having the above configuration, for example, when the shaft (1) is rotated, dynamic pressure in the radial direction is generated in the lubricating oil composition in the minute gaps by the dynamic pressure grooves (3) and (4), and dynamic pressure in the axial direction (thrust force) is also generated in the lubricating oil composition in the minute gaps by the bearing surface; these dynamic pressures cause the shaft (1) with the thrust plate (7) to rotate at high speed while not in contact with the sleeve (2) and counter plate (8).

The fluid bearing of the present invention uses as the lubricating oil (9) the lubricating oil composition for a bearing, which contains the lubricating base oil for a fluid bearing having good stability, viscosity properties, low-temperature properties, and volatility resistance; thus, bearing life longer than that of a fluid bearing using a conventional lubricating oil composition can be obtained without increasing the amount of the lubricating oil composition retained. The fluid bearing of the present invention is thus suitable as a fluid bearing applied to, for example, spindle motors, which are required to be compact, have high accuracy, and rotate at high speed.

Spindle Motor

Figure 19:
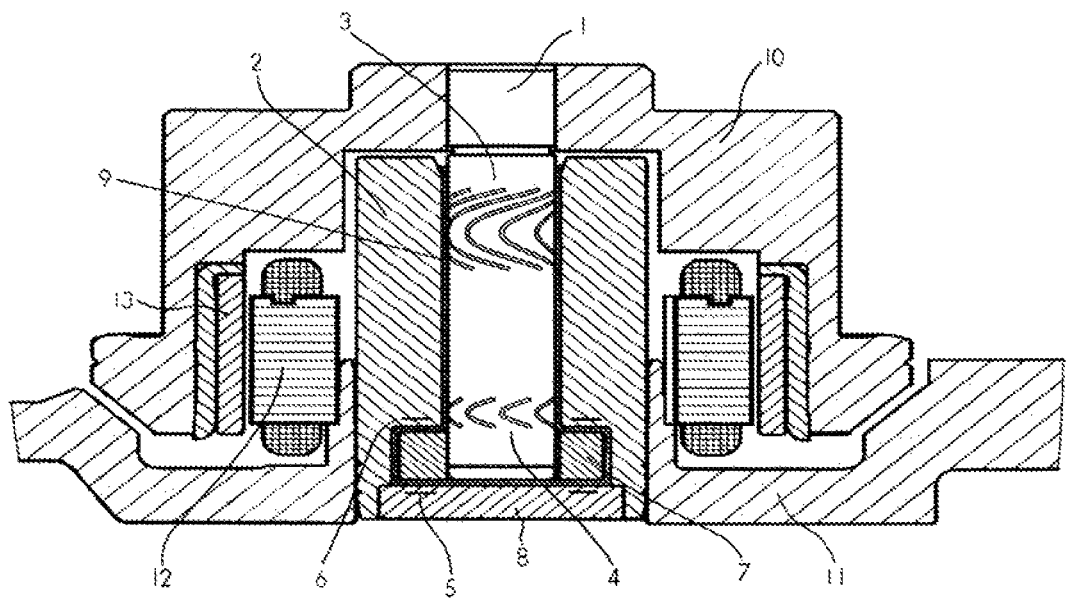
FIG. 19 illustrates an example of the cross-sectional surface of the spindle motor according to the present invention.

The present invention also provides a spindle motor comprising the fluid bearing described above. Specific examples of the spindle motor of the present invention include the spindle motor shown in FIG. 19. FIG. 19 is an example of a cross-sectional view schematically showing an outline configuration of the spindle motor of the present invention.

In the spindle motor of the present invention, a motor drive unit is configured such that a stator coil (12) is provided on a wall formed on a base (11), and such that a rotor magnet (13) is attached on the inner peripheral surface of a hub (10) so as to face the stator coil (12). When the rotating part is rotated by the motor drive unit, dynamic pressure is generated in both the radial direction and the thrust direction in the lubricating oil composition (9), thus maintaining the rotation with the rotating part and the fixed part not in contact with each other.

EXAMPLES

The present invention is described below in detail with reference to Examples; however, the present invention is not limited to these Examples. The physical properties and chemical properties of the lubricating base oils for a fluid bearing and lubricating oil compositions for a fluid bearing in the Examples were evaluated by the following methods. Compounds used in the Examples without specific description are reagents.

Compounds

Raw Materials

2-Methylpentanoic acid (produced by Tokyo Chemical Industry Co., Ltd.)

2-Methylbutanoic acid (produced by Fujifilm Wako Pure Chemical Corporation)

2-Decyltetradecanol: NJCOL 240A (produced by New Japan Chemical Co., Ltd.)

2-Octyldodecanol: ISOFOL 20 (produced by Sasol)

2-Hexyldecanol: ISOFOL 16 (produced by Sasol)

Antioxidants

Amine-based antioxidant p,p'-dioctyl diphenylamine: bis(4-octylphenyl)amine (produced by Ark Pharm, Inc.; referred to below as "DODPA")

Phenolic antioxidant 4,4'-methylenebis(2,6-di-tert-butylphenol) (produced by Tokyo Chemical Industry Co., Ltd.; referred to below as "MBDBP")

(a) Acid Value

Measurement was performed according to JIS-K-2501 (2003). The detection limit was 0.01 mg KOH/g.

(b) Purity of 2-Methyl Fatty Acid (Raw Material)

Analysis by Gas Chromatography (GC)

The purity of 2-methyl fatty acid (GC area %) was measured by gas chromatography (GC).

Measurement Conditions

Instrument: Shimadzu Corporation GC-2010

Column: TC-5, 30 m×0.25 mm×0.25 µm (produced by GL Sciences Inc.)

Column Temperature: 60 to 300° C. (temperature increase rate: 10° C./min)

Injection Temperature/Detector Temperature: 305° C./305° C.

Detector: FID

Carrier Gas: Helium

Gas Linear Velocity: 27.4 cm/sec

Sample: 1 Mass % Acetone Solution

Injection Amount: 1 µl (c) Kinematic Viscosity

The kinematic viscosity at 40° C. and 100° C. was measured according to JIS-K-2283 (2000).

Evaluation of Kinematic Viscosity at 40° C.

(I): 10 mm$^2$/s or more and less than 14 mm$^2$/s (II): 8 mm$^2$/s or more and less than 10 mm$^2$/s; or 14 mm$^2$/s or more and less than 17 mm$^2$/s (III): less than 8 mm$^2$/s or 17 mm$^2$/s or more (d) Viscosity Index The viscosity index was calculated according to JIS-K-2283 (2000). A viscosity index of 140 or more is evaluated as indicating excellent viscosity-temperature characteristics.

Evaluation of Viscosity Index (I): 140 or more (II): 130 or more and less than 140

(III): less than 130

(e) Evaporation Resistance About 10 mg of the lubricating base oil for a fluid bearing or the lubricating oil composition for a fluid bearing was accurately weighed (to the third decimal place), and placed in a TG-DTA device (produced by SII Nano-Technology Inc., device name: TG/DTA6200). The temperature at which the mass was reduced by 5% from the initial mass (temperature at which the mass was reduced by 5%) under the following measurement conditions was used as an index of evaporation resistance.
Measurement Conditions
Temperature increase rate: 10° C./min
Circulated nitrogen amount: 200 ml/min
Measurement start temperature: 50° C.
Evaluation of Evaporation Resistance (Temperature at which the Mass was Reduced by 5%)
(I): 260° C. or more
(II): 250° C. or more, and less than 260° C.
(III): less than 250° C.
(f) Hydrolytic Stability Test A hydrolysis test was performed in the following manner. 2 g of a lubricating base oil for a fluid bearing or a lubricating oil composition for a fluid bearing, and 0.2 g of ion-exchanged water were weighed into a stainless-steel pressure-resistant container. After being freeze-degassed and nitrogen-purged, the pressure-resistant container was sealed. After the sealed stainless-steel pressure-resistant container was allowed to stand in a Fine Oven at 160° C. for 24 hours, the test liquid was fully removed from the test tube, and the acid value was measured. As an index of hydrolytic stability, the increase in acid value between before and after the hydrolysis test was calculated.
Evaluation of Hydrolytic Stability (Increase in Acid Value)
(I): 0.15 mg KOH/g or less
(II): over 0.15 mg KOH/g and 0.5 mg KOH/g or less
(III): over 0.5 mg KOH/g
(g) Melting Point 5 μL of 2-methyl aliphatic monocarboxylic acid ester was precisely weighed and set to a differential scanning calorimeter (DSC6220, produced by SII NanoTechnology Inc.), followed by cooling to −65° C. Measurement was performed under the following measurement conditions.
Measurement Conditions
Temperature increase rate: 1° C./min
Circulated nitrogen amount: 50 ml/min
Measurement temperature range: −65° to 20° C.
Evaluation of Low-Temperature Fluidity (Melting Point)
(I): −10° C. or less
(II): over −10° C. and 0° C. or less
(III): over 0° C.
(h) Evaluation of Lubricating Base Oil for Fluid Bearing The lubricating base oil for a fluid bearing and the lubricating oil composition for a fluid bearing were evaluated as follows. In the results of evaluation of kinematic viscosity at 40° C., evaluation of viscosity index, evaluation of evaporation resistance, evaluation of hydrolytic stability, and evaluation of low-temperature fluidity, if 1 or more results were rated (III), the oil or the composition was evaluated as unsuitable; if 1 or less results were rated (II) (being rated (I) in other evaluations), the oil or the composition was evaluated as good; and if all results were rated (I), the oil or the composition was evaluated as particularly good.
Infrared Absorption Spectrum (IR Spectrum)

The IR spectrum of 2-methyl aliphatic monocarboxylic acid ester was measured with an infrared spectrophotometer (Spectrum400, produced by PerkinElmer Japan Co., Ltd.) by an attenuated total reflection (ATR) method.
Proton Nuclear Magnetic Resonance Spectrum ($^1$H-NMR)

$^1$H-NMR of 2-methyl aliphatic monocarboxylic acid ester was measured by dissolving it in deuterated chloroform, by using a nuclear magnetic resonator (DRX-500, produced by Bruker) by $^1$H-NMR measurement (500 MHz).

Production Example 1

(2-Methylheptanoic Acid)

Referring to the Journal of Chemical Ecology, 37(7), 714-716, 2011, 2-methylheptanoic acid was synthesized. 3.44 mol of sodium ethoxide and 1.5 L of ethanol were placed in a 5-L four-necked flask equipped with a stirrer, a thermometer, a cooling pipe, and a dropping funnel, and then 2.87 mol of diethyl methylmalonate was added dropwise thereto at room temperature. Subsequently, 2.87 mol of 1-bromopentane was added; after completion of the dropwise addition, the mixture was refluxed under ordinary pressure for 3 hours. After reflux, ethanol was distilled off, and sodium bromide was removed by washing with water. Two equivalents of potassium hydroxide based on the added diethyl methylmalonate were formed into an aqueous solution and added, followed by performing hydrolysis while ethanol forming at 95° C. was distilled off. A 10% aqueous sulfuric acid solution was added to the obtained aqueous potassium salt solution to neutralize it at room temperature, and the precipitated dicarboxylic acid was filtered, followed by washing with water. The obtained hydrous powder of dicarboxylic acid was placed in a 3-L four-necked flask equipped with a stirrer, a thermometer, and a water fraction receiver with a cooling pipe, and gradually heated to 160° C. to dissolve the powder, followed by decarboxylation until no foaming was observed, thereby obtaining a crude product of monocarboxylic acid. The obtained crude product was rectified, thereby obtaining 2-methylheptanoic acid with a purity of 99.6 GC area % at a yield of 66%.

Production Example 2

(2-Methyloctanoic Acid)

2-Methyloctanoic acid with a purity of 99.5 GC area % was obtained at a yield of 70% in the same manner as in Production Example 1 except that 1-bromohexane was used instead of 1-bromopentane.

Production Example 3

(2-Methylundecanoic Acid)

2-Methylundecanoic acid with a purity of 99.7 GC area % was obtained at a yield of 71% in the same manner as in Production Example 1 except that 1-bromononane was used instead of 1-bromopentane.

Production Example 4

(2-Methylhexadecanoic Acid)

2-Methylhexadecanoic acid with a purity of 99.4 GC area % was obtained at a yield of 52% in the same manner as in Production Example 1 except that 1-bromotetradecane was used instead of 1-bromopentane.

Production Example 5

(2-Methylnonanoic Acid)

2-Methylnonanoic acid with a purity of 99.6 GC area % was obtained at a yield of 66% in the same manner as in Production Example 1 except that 1-bromoheptane was used instead of 1-bromopentane.

Production Example 6

(A Mixture of 2-Pentylhexadecanol and 2-Heptyltetradecanol (50:50))

Referring to JPS49-035308A, an alcohol dimerization reaction was performed using 1-tetradecanol and 1-heptanol. Specifically, 9.34 mol of 1-tetradecanol, 9.34 mol of 1-heptanol, 92.0 g of potassium hydroxide, 6.2 g of a copper chromium catalyst, and 18.6 g of activated carbon were added, and a dimerization reaction was carried out at 250° C. After the reaction, the copper chromium catalyst, activated carbon, and carboxylic acid potassium salt were removed by filtration to obtain a crude product containing four dimerized alcohols, i.e., 2-pentylnonanol, 2-pentylhexadecanol, 2-heptyltetradecanol, and 2-dodecylhexadecanol.

The obtained crude dimerized alcohol product was subjected to rectification to collect 2-pentylnonanol as a pre-fraction, and 2-heptyldecanol and then 2-pentylhexadecanol as main fractions. The obtained 2-pentylhexadecanol and 2-heptyltetradecanol were mixed at a desired ratio, and the mixture was used as an ester raw material described below.

Example 1

0.432 mol of 2-methylpentanoic acid, 0.404 mol of 2-decyltetradecanol, xylene (20 mass % relative to the total amount of raw materials), and a tin oxide catalyst (0.1 mass % relative to the total amount of raw materials) as a catalyst were placed in a 500-mL four-necked flask equipped with a stirrer, a thermometer, and a water fraction receiver with a cooling pipe. After purging with nitrogen, the mixture was gradually heated to 220° C. An esterification reaction was performed while removing distilled water using the water fraction receiver with reference to the theoretical water amount (7.28 g), and adjusting the decompression degree so that reflux occurred. The reaction was performed until the theoretical amount of water was distilled.

After completion of the reaction, xylene was removed by distillation to obtain a crude esterified product. After neutralization with 2 equivalents of a caustic soda aqueous solution relative to the acid value of the obtained crude esterified product, water washing was repeated until the washing water was neutral. Furthermore, after the obtained crude esterified product was subjected to adsorption treatment with activated carbon, the activated carbon was removed by filtration, thereby obtaining 2-decyltetradecyl 2-methylpentanoate.

The acid value was no more than 0.01 mg KOH/g.

The obtained 2-decyltetradecyl 2-methylpentanoate, which is referred to as "ester A," was evaluated as a lubricating base oil for a fluid bearing. Table 1 shows the results.

Figure 2:
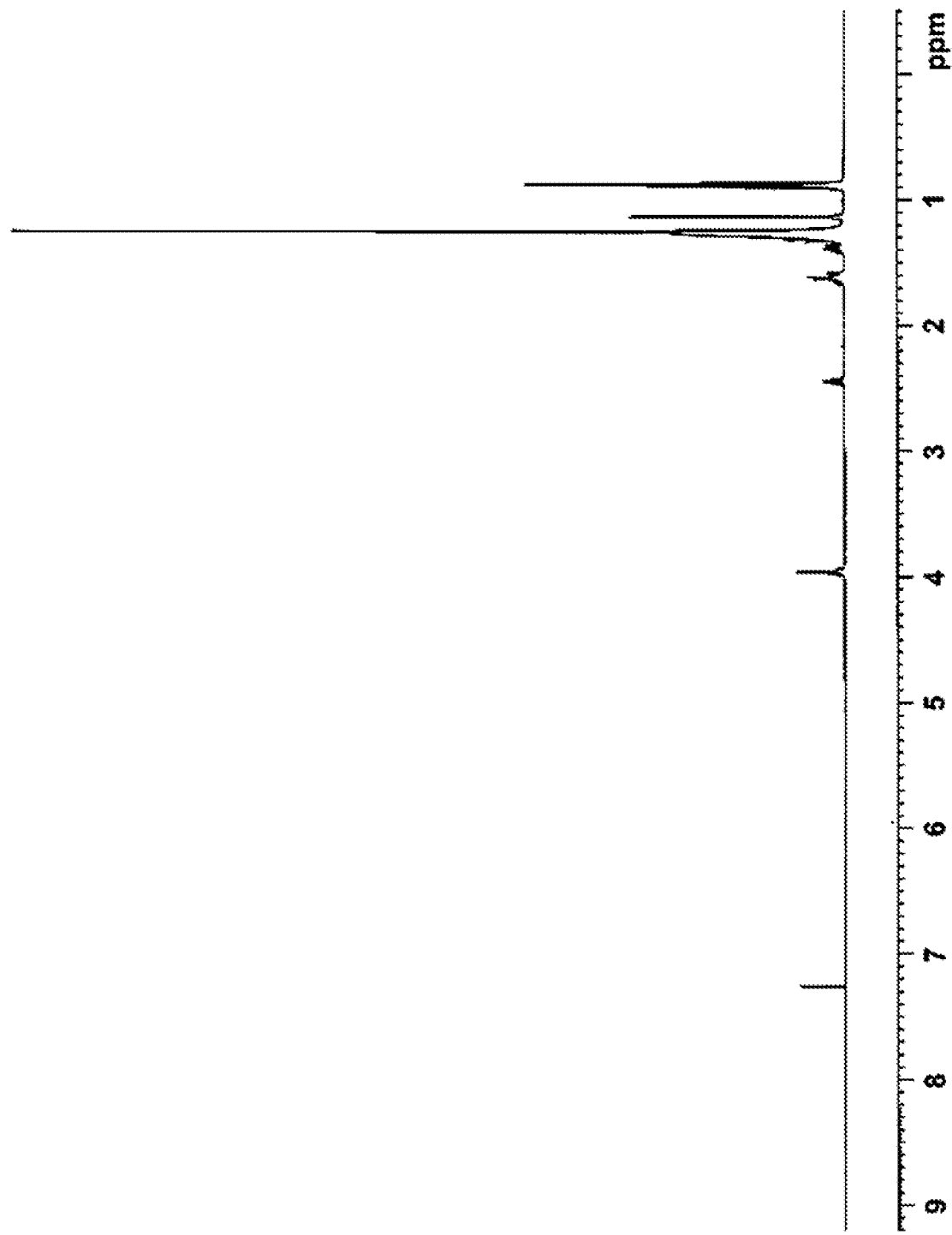
FIG. 2 illustrates a 1H-NMR spectrum of 2-decyltetradecyl 2-methylpentanoate obtained in Example 1.

The IR spectrum and $^1$H-NMR spectrum of 2-decyltetradecyl 2-methylpentanoate were measured and are shown in FIGS. 1 and 2. In the $^1$H-NMR spectrum, the singlet peak around 7.26 ppm is derived from deuterated chloroform (solvent), and the singlet peak around 1.58 ppm is derived from water contained in the deuterated chloroform (solvent).

IR (cm$^{-1}$): 2957, 2922, 2853, 1735, 1465, 1378, 1272, 1242, 1176, 1148, 1084, 1053, 1032, 928, 721

$^1$H-NMR (500 MHz, ppm): 0.87-0.92 (m, 9H), 1.13-1.15 (d, 3H), 1.26-1.42 (m, 43H), 1.60-1.68 (m, 2H), 2.41-2.48 (m, 1H), 3.93-3.99 (m, 2H)

Example 2

2-Decyltetradecyl 2-methylheptanoate with an acid value of 0.01 mg KOH/g or less was obtained in the same manner as in Example 1 except that 2-methylheptanoic acid was used instead of 2-methylpentanoic acid. The obtained 2-decyltetradecyl 2-methylheptanoate ("ester (B)") was then evaluated as a lubricating base oil for a fluid bearing. Table 1 illustrates the results.

Figure 3:
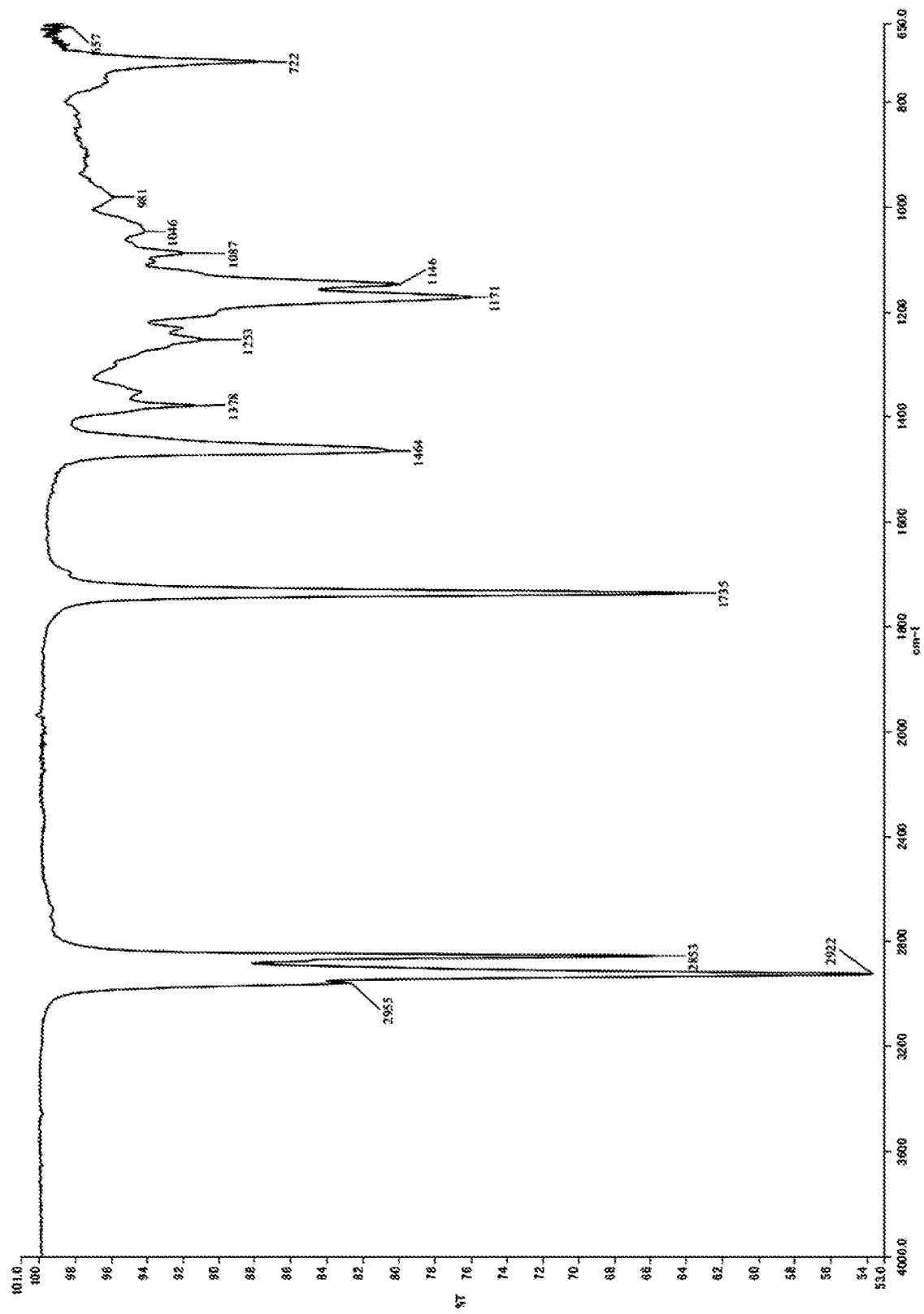
FIG. 3 illustrates an IR spectrum of 2-decyltetradecyl 2-methylheptanoate obtained in Example 2.
Figure 4:
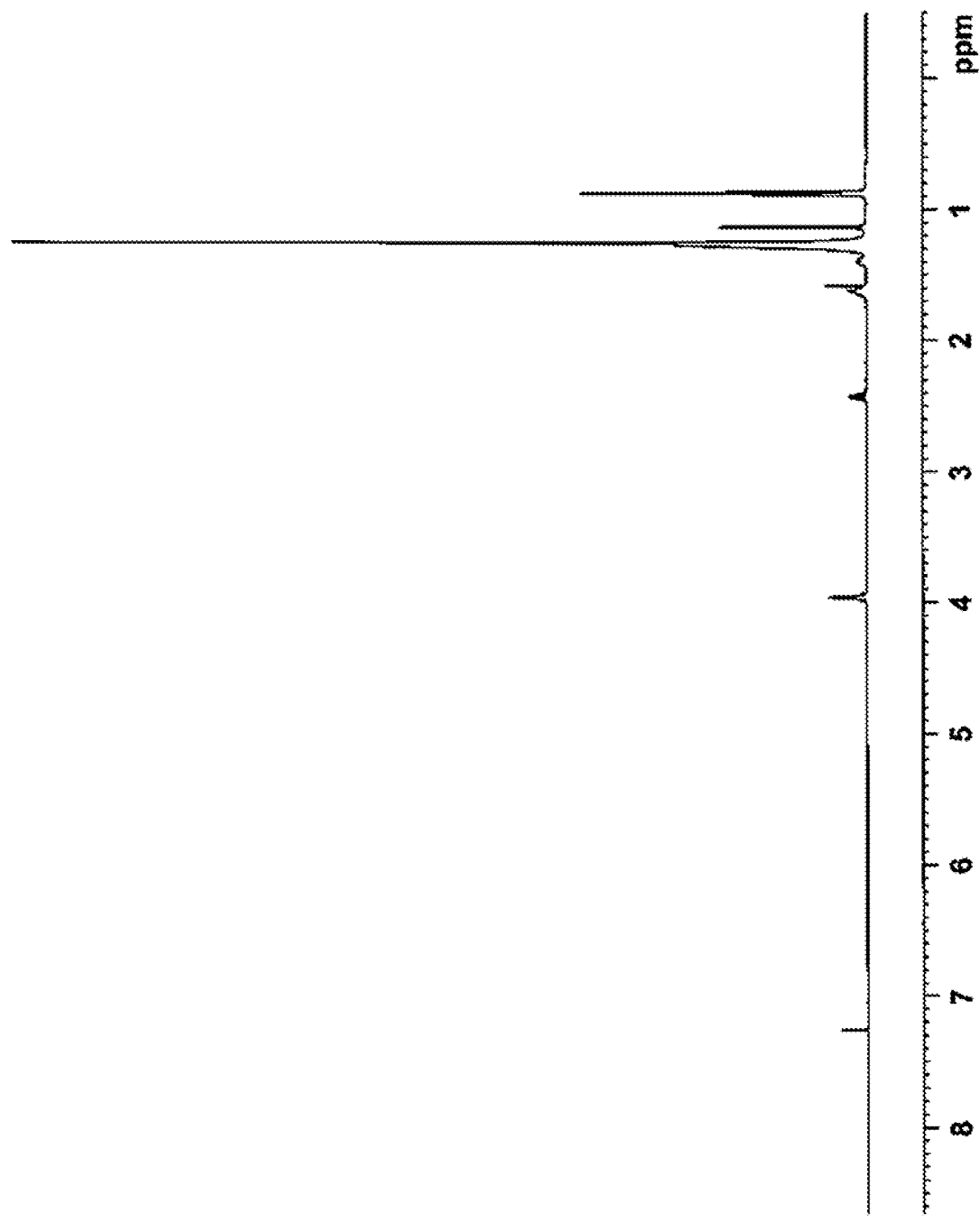
FIG. 4 illustrates a 1H-NMR spectrum of 2-decyltetradecyl 2-methylheptanoate obtained in Example 2.

An IR spectrum and a 1H-NMR spectrum of 2-decyltetradecyl 2-methylheptanoate were measured, and FIGS. 3 and 4 illustrate the spectra. In the $^1$H-NMR spectrum, the singlet peak around 7.26 ppm is derived from deuterated chloroform (solvent), and the singlet peak around 1.58 ppm is derived from water contained in the deuterated chloroform (solvent).

IR (cm$^{-1}$): 2955, 2922, 2853, 1735, 1464, 1378, 1253, 1171, 1146, 1087, 1046, 981, 722, 657

$^1$H-NMR (500 MHz, ppm): 0.87-0.89 (m, 9H), 1.13-1.15 (d, 3H), 1.26-1.28 (m, 46H), 1.37-1.42 (m, 1H), 1.61-1.67 (m, 2H), 2.40-2.46 (m, 1H), 3.93-4.00 (m, 2H)

Example 3

2-Decyltetradecyl 2-methyloctanoate with an acid value of 0.01 mg KOH/g or less was obtained in the same manner as in Example 1 except that 2-methyloctanoic acid was used instead of 2-methylpentanoic acid. The obtained 2-decyltetradecyl 2-methyloctanoate ("ester (C)") was then evaluated as a lubricating base oil for a fluid bearing. Table 1 illustrates the results.

Figure 5:
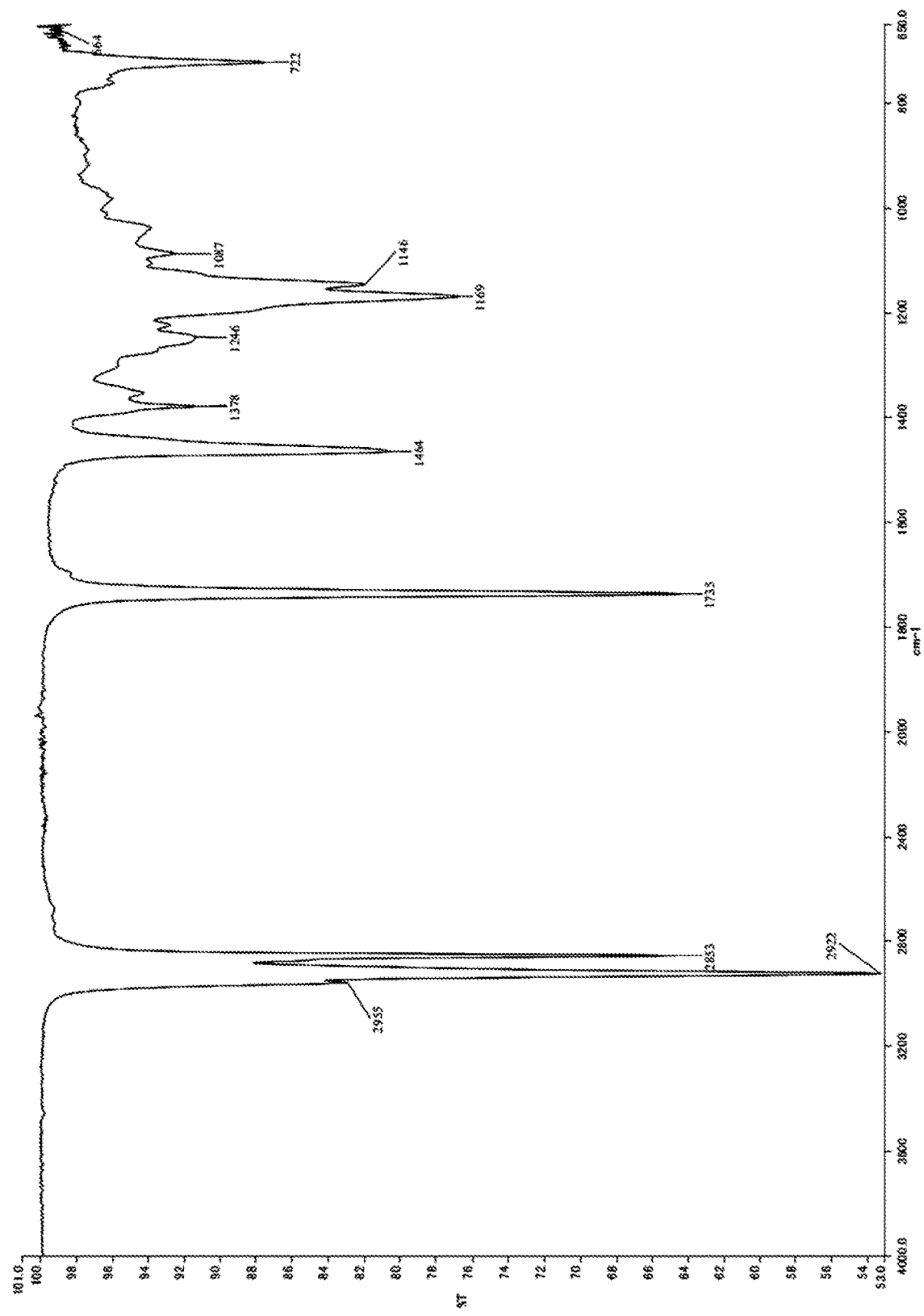
FIG. 5 illustrates an IR spectrum of 2-decyltetradecyl 2-methyloctanoate obtained in Example 3.
Figure 6:
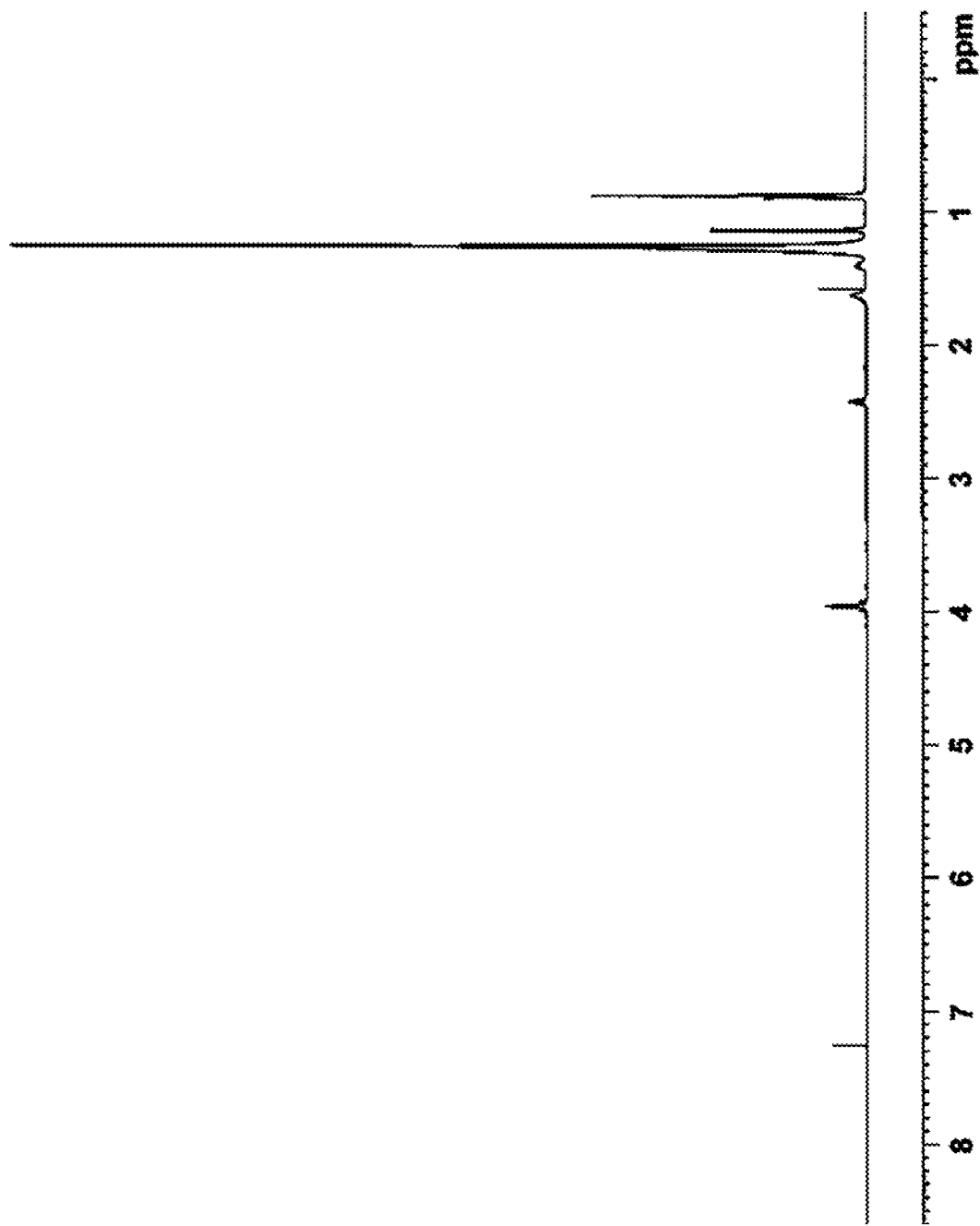
FIG. 6 illustrates a 1H-NMR spectrum of 2-decyltetradecyl 2-methyloctanoate obtained in Example 3.

An IR spectrum and a 1H-NMR spectrum of 2-decyltetradecyl 2-methyloctanoate were measured, and FIGS. 5 and 6 illustrate the spectra. In the 1H-NMR spectrum, the singlet peak around 7.26 ppm is derived from deuterated chloroform (solvent), and the singlet peak around 1.58 ppm is derived from water contained in the deuterated chloroform (solvent).

IR (cm$^{-1}$): 2955, 2922, 2853, 1735, 1464, 1378, 1246, 1169, 1146, 1087, 1046, 981, 722, 657

$^1$H-NMR (500 MHz, ppm): 0.87-0.89 (m, 9H), 1.13-1.14 (d, 3H), 1.26-1.28 (m, 48H), 1.37-1.44 (m, 1H), 1.61-1.68 (m, 2H), 2.39-2.46 (m, 1H), 3.93-4.00 (m, 2H)

Example 4

2-Octyldodecyl 2-methylundecanoate with an acid value of 0.01 mg KOH/g or less was obtained in the same manner as in Example 1 except that 2-methylundecanoic acid was used instead of 2-methylpentanoic acid, and that 2-octyldodecanol was used instead of 2-decyltetradecanol. The obtained 2-octyldodecyl 2-methylundecanoate ("ester (D)") was evaluated as a lubricating base oil for a fluid bearing. Table 1 illustrates the results.

Figure 7:
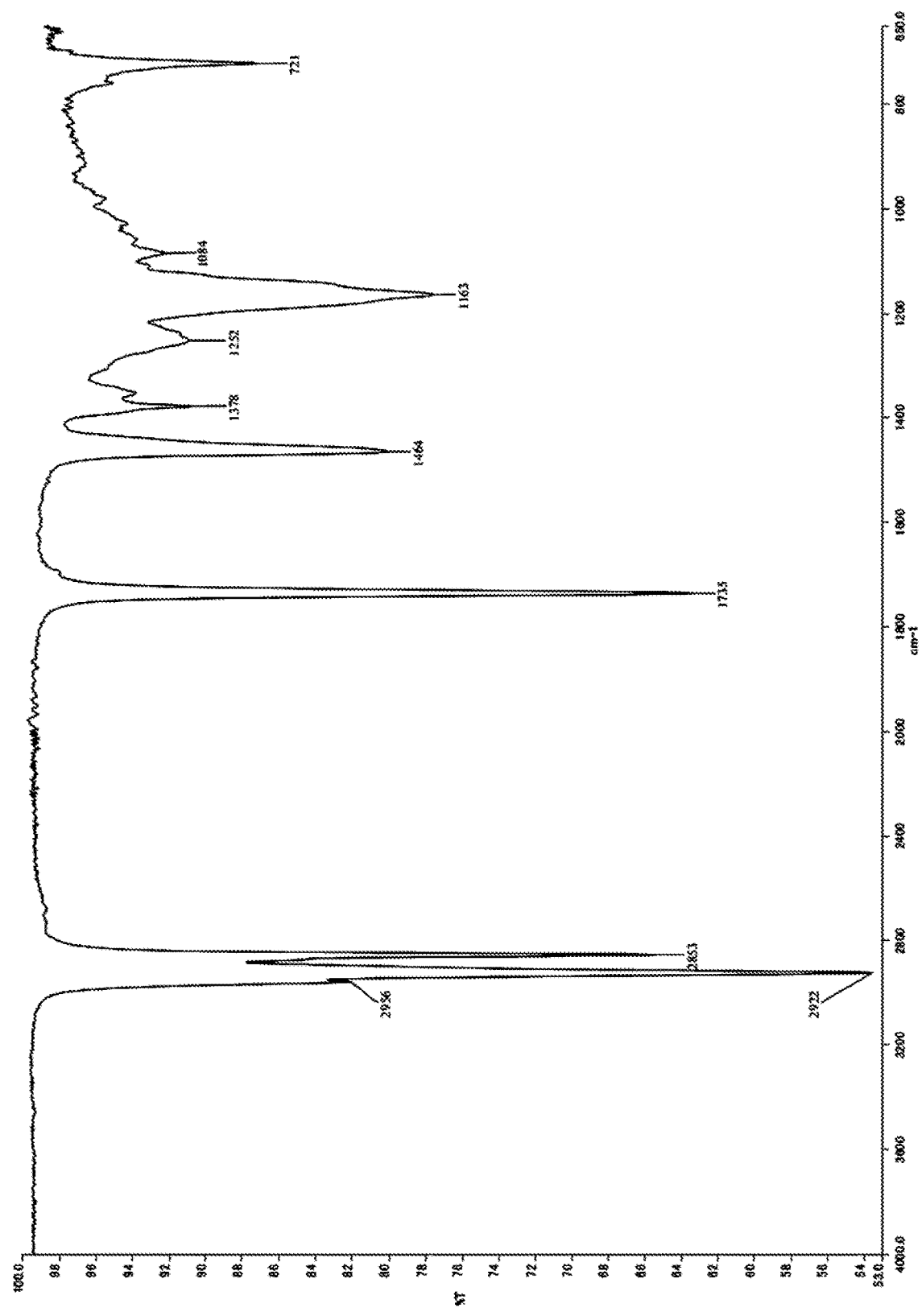
FIG. 7 illustrates an IR spectrum of 2-octyldodecyl 2-methylundecanoate obtained in Example 4.
Figure 8:
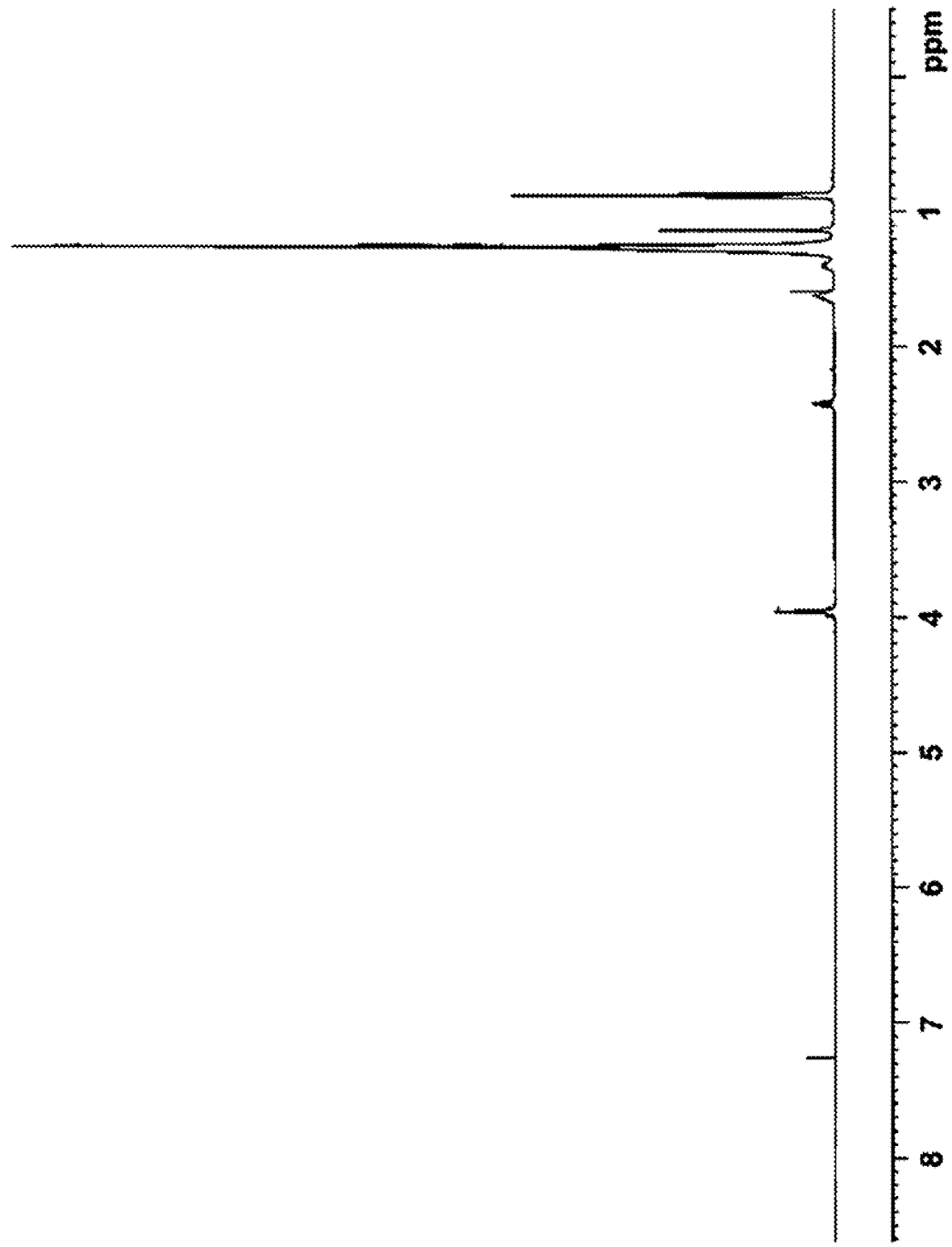
FIG. 8 illustrates a 1H-NMR spectrum of 2-octyldodecyl 2-methylundecanoate obtained in Example 4.

An IR spectrum and a 1H-NMR spectrum of 2-octyldodecyl 2-methylundecanoate were measured, and FIGS. 7 and 8 illustrate the spectra. In the $^1$H-NMR spectrum, the singlet peak around 7.26 ppm is derived from deuterated chloroform (solvent), and the singlet peak around 1.58 ppm is derived from water contained in the deuterated chloroform (solvent).

IR (cm$^{-1}$): 2956, 2922, 2853, 1735, 1464, 1378, 1252, 1163, 1084, 721

$^1$H-NMR (500 MHz, ppm): 0.87-0.89 (m, 9H), 1.13-1.14 (d, 3H), 1.26-1.28 (m, 46H), 1.37-1.42 (m, 1H), 1.62-1.68 (m, 2H), 2.39-2.46 (m, 1H), 3.93-4.00 (m, 2H)

Example 5

2-Hexyldecyl 2-methylhexadecanoate with an acid value of 0.01 mg KOH/g or less was obtained in the same manner as in Example 1 except that 2-methylhexadecanoic acid was used instead of 2-methylpentanoic acid, and that 2-hexyldecanol was used instead of 2-decyltetradecanol. The obtained 2-hexyldecyl 2-methylhexadecanoate ("ester (E)") was then evaluated as a lubricating base oil for a fluid bearing. Table 1 illustrates the results.

Figure 9:
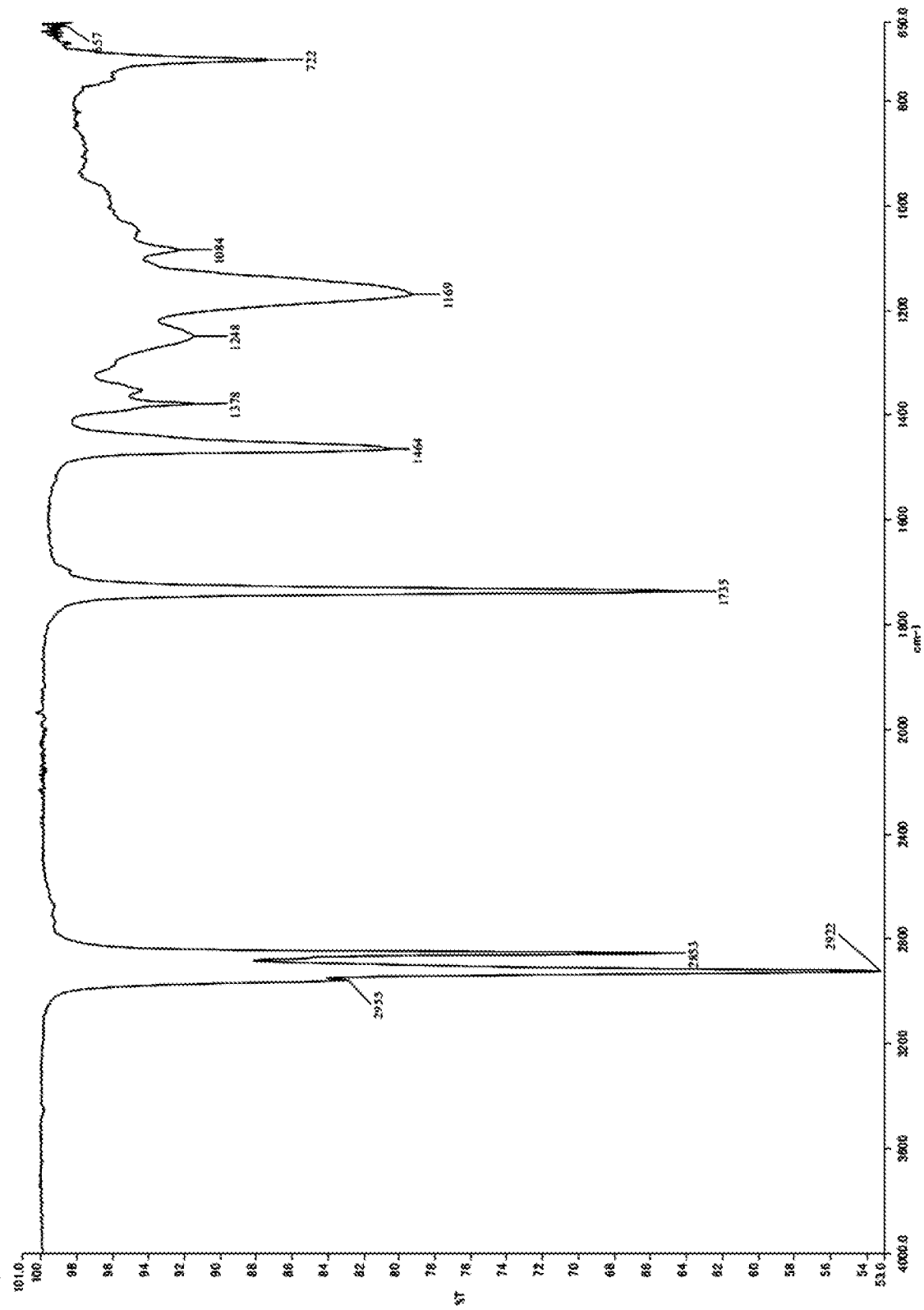
FIG. 9 illustrates an IR spectrum of 2-hexyldecyl 2-methylhexadecanoate obtained in Example 5.
Figure 10:
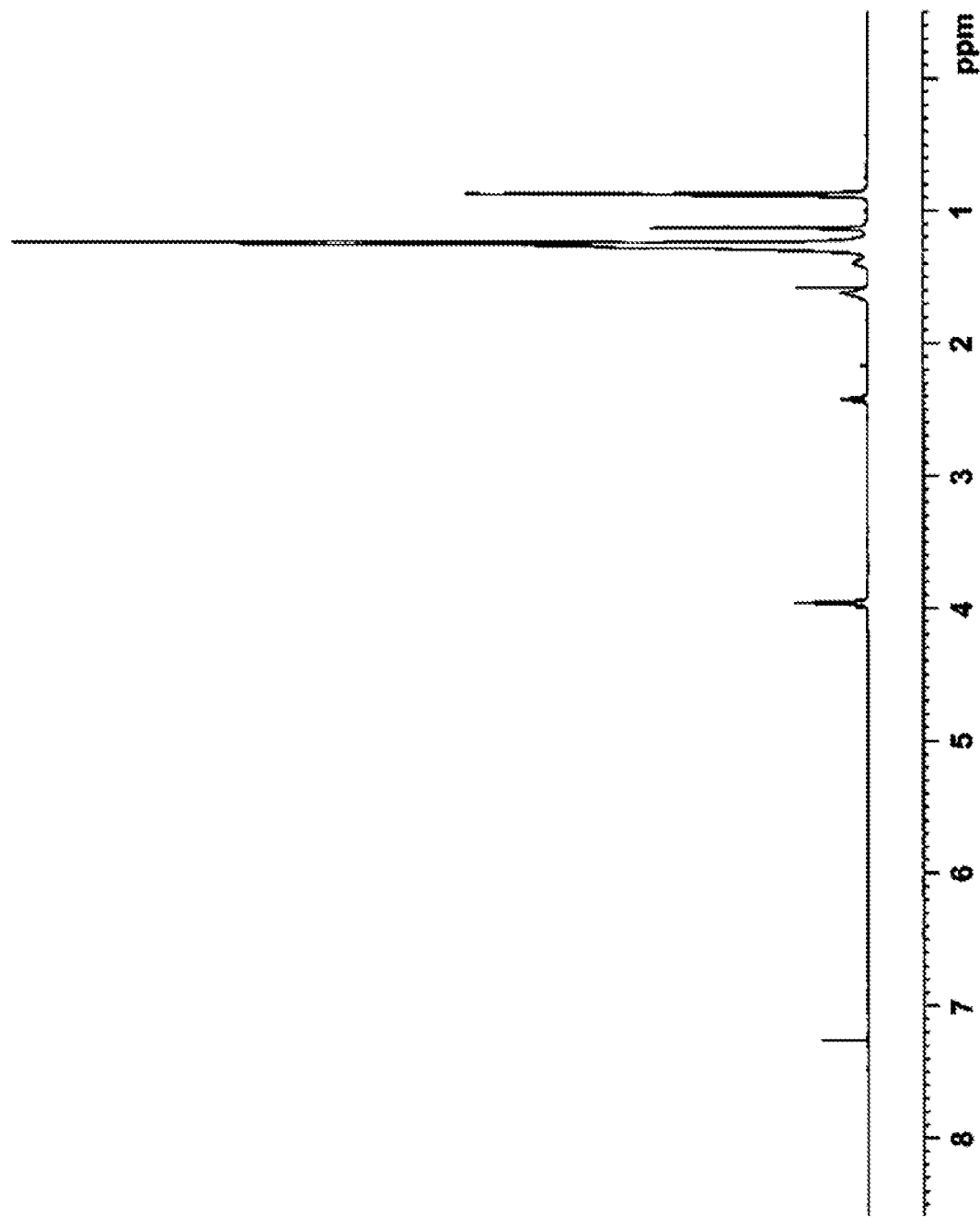
FIG. 10 illustrates a 1H-NMR spectrum of 2-hexyldecyl 2-methylhexadecanoate obtained in Example 5.

An IR spectrum and a 1H-NMR spectrum of 2-hexyldecyl 2-methylhexadecanoate were measured, and FIGS. 9 and 10 illustrate the spectra. In the $^1$H-NMR spectrum, the singlet peak around 7.26 ppm is derived from deuterated chloroform (solvent), and the singlet peak around 1.58 ppm is derived from water contained in the deuterated chloroform (solvent).

IR (cm$^{-1}$): 2955, 2922, 2853, 1735, 1464, 1378, 1248, 1169, 1084, 722, 657

$^1$H-NMR (500 MHz, ppm): 0.87-0.89 (m, 9H), 1.13-1.14 (d, 3H), 1.25-1.28 (m, 48H), 1.37-1.42 (m, 1H), 1.62-1.66 (m, 2H), 2.39-2.46 (m, 1H), 3.93-4.00 (m, 2H)

Example 6

2-Decyltetradecyl 2-methylbutanoate with an acid value of 0.01 KOH/g or less was obtained in the same manner as in Example 1 except that 2-methylbutanoic acid was used instead of 2-methylpentanoic acid. The obtained 2-decyltetradecyl 2-methylbutanoate ("ester (F)") was then evaluated as a lubricating base oil for a fluid bearing. Table 1 illustrates the results.

Figure 11:
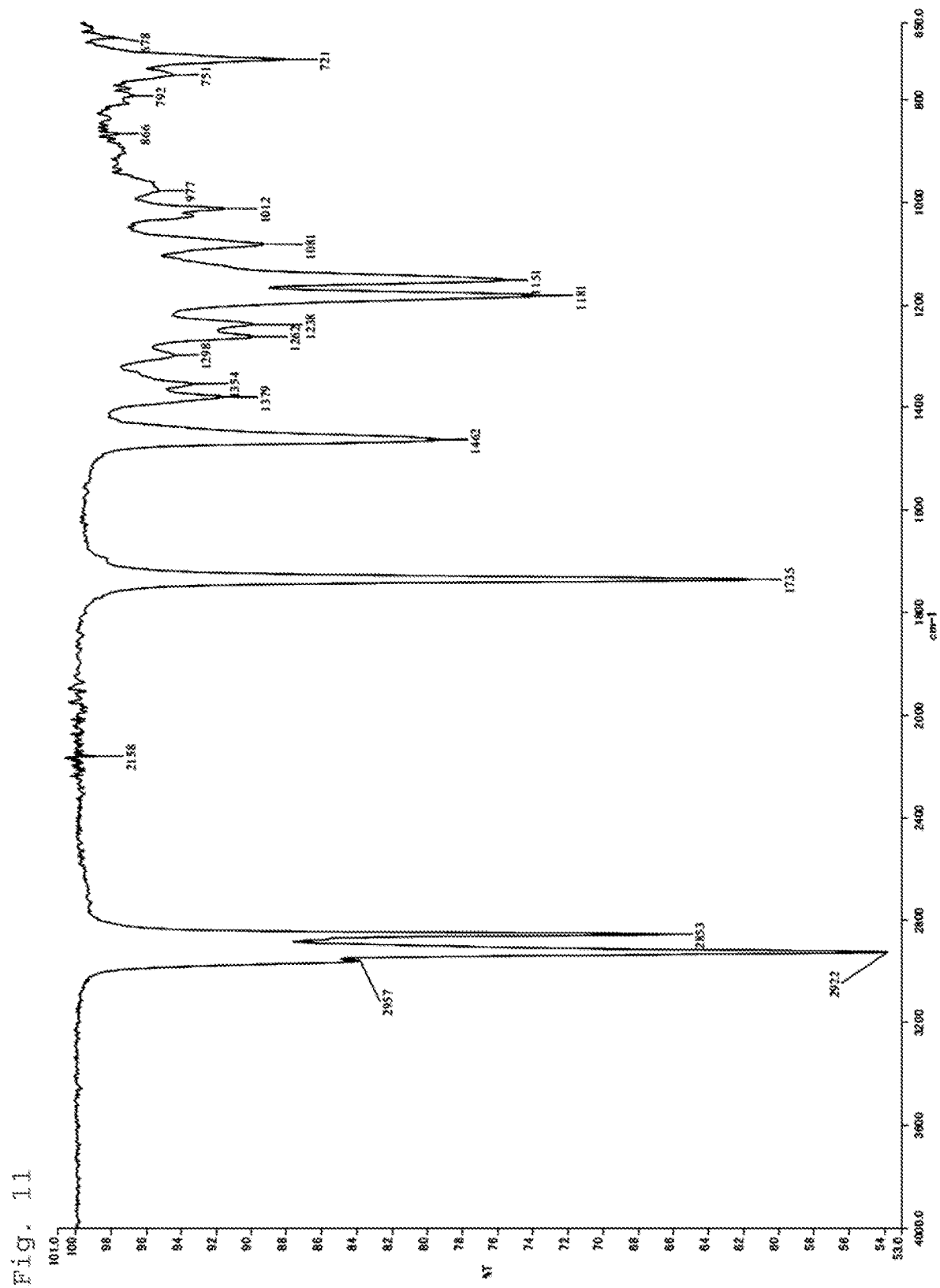
FIG. 11 illustrates an IR spectrum of 2-decyltetradecyl 2-methylbutanoate obtained in Example 6.
Figure 12:
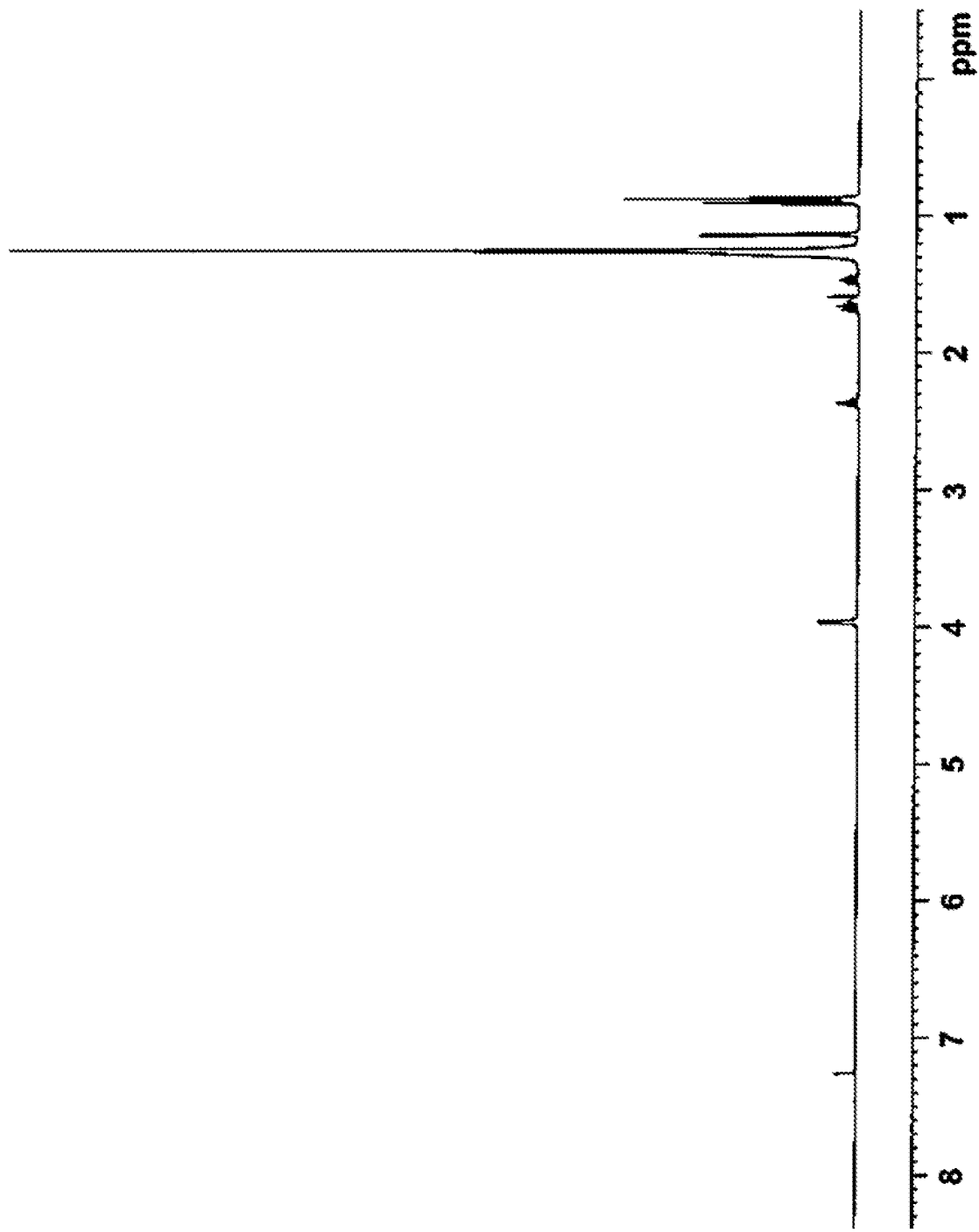
FIG. 12 illustrates a 1H-NMR spectrum of 2-decyltetradecyl 2-methylbutanoate obtained in Example 6.

An IR spectrum and a 1H-NMR spectrum of 2-decyltetradecyl 2-methylbutanoate were measured, and FIGS. 11 and 12 illustrate the spectra. In the $^1$H-NMR spectrum, the singlet peak around 7.26 ppm is derived from deuterated chloroform (solvent), and the singlet peak around 1.59 ppm is derived from water contained in the deuterated chloroform (solvent).

IR (cm$^{-1}$): 2957, 2922, 2853, 2158, 1735, 1462, 1379, 1354, 1298, 1262, 1238, 1181, 1151, 1081, 1012, 977, 866, 792, 751, 721, 678

$^1$H-NMR (500 MHz, ppm): 0.87-0.92 (m, 9H), 1.13-1.15 (d, 3H), 1.26-1.28 (m, 40H), 1.43-1.51 (m, 1H), 1.62-1.72 (m, 2H), 2.33-2.40 (m, 1H), 3.94-4.00 (m, 2H)

Example 7

2-Octyldodecyl 2-methyloctanoate with an acid value of 0.01 KOH/g or less was obtained in the same manner as in Example 1 except that 2-methyloctanoic acid was used instead of 2-methylpentanoic acid, and that 2-octyldodecanol was used instead of 2-decyltetradecanol. The obtained 2-octyldodecyl 2-methyloctanoate ("ester (G)") was then evaluated as a lubricating base oil for a fluid bearing. Table 1 illustrates the results.

Figure 13:
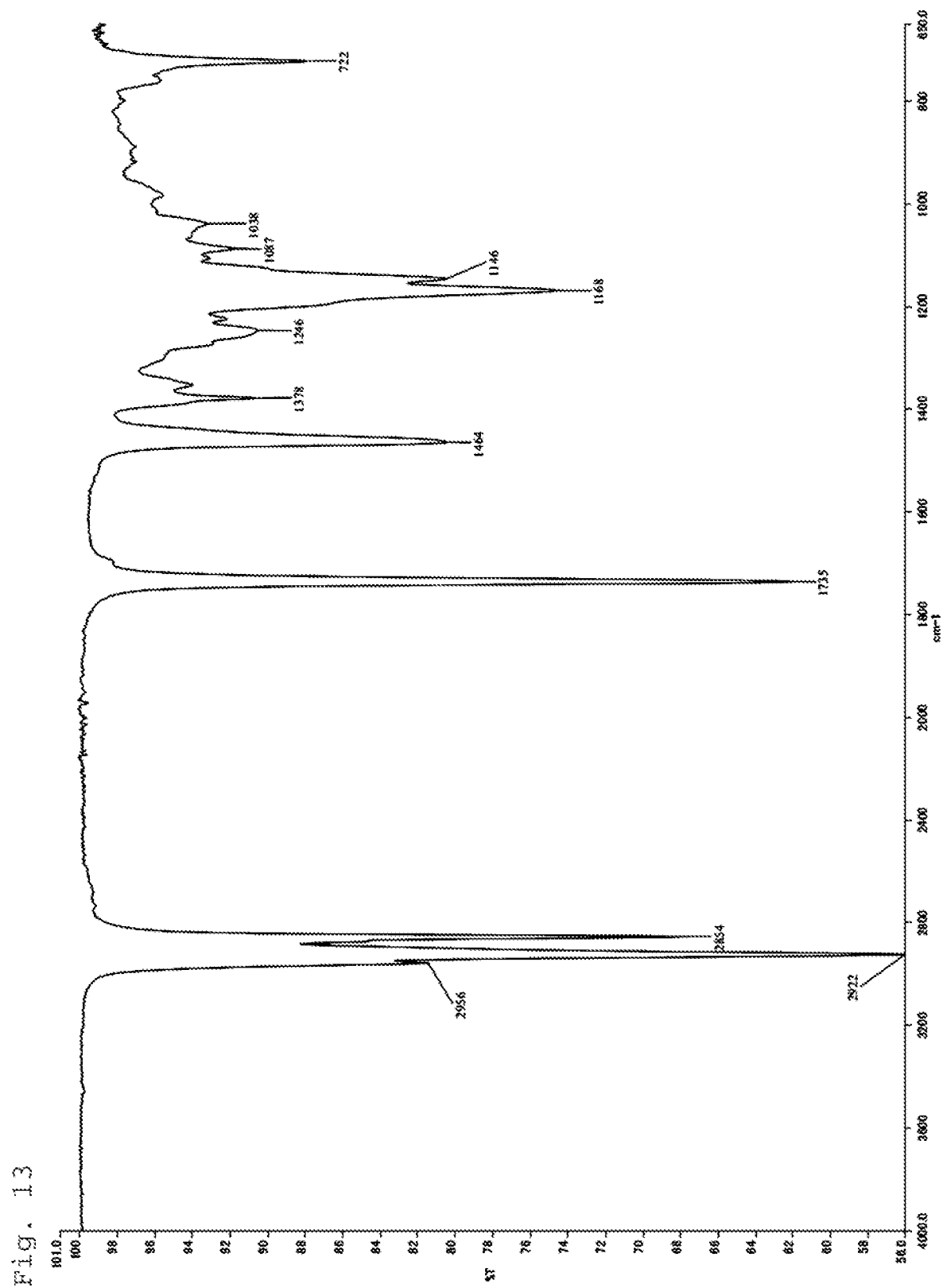
FIG. 13 illustrates an IR spectrum of 2-octyldodecyl 2-methyloctanoate obtained in Example 7.
Figure 14:
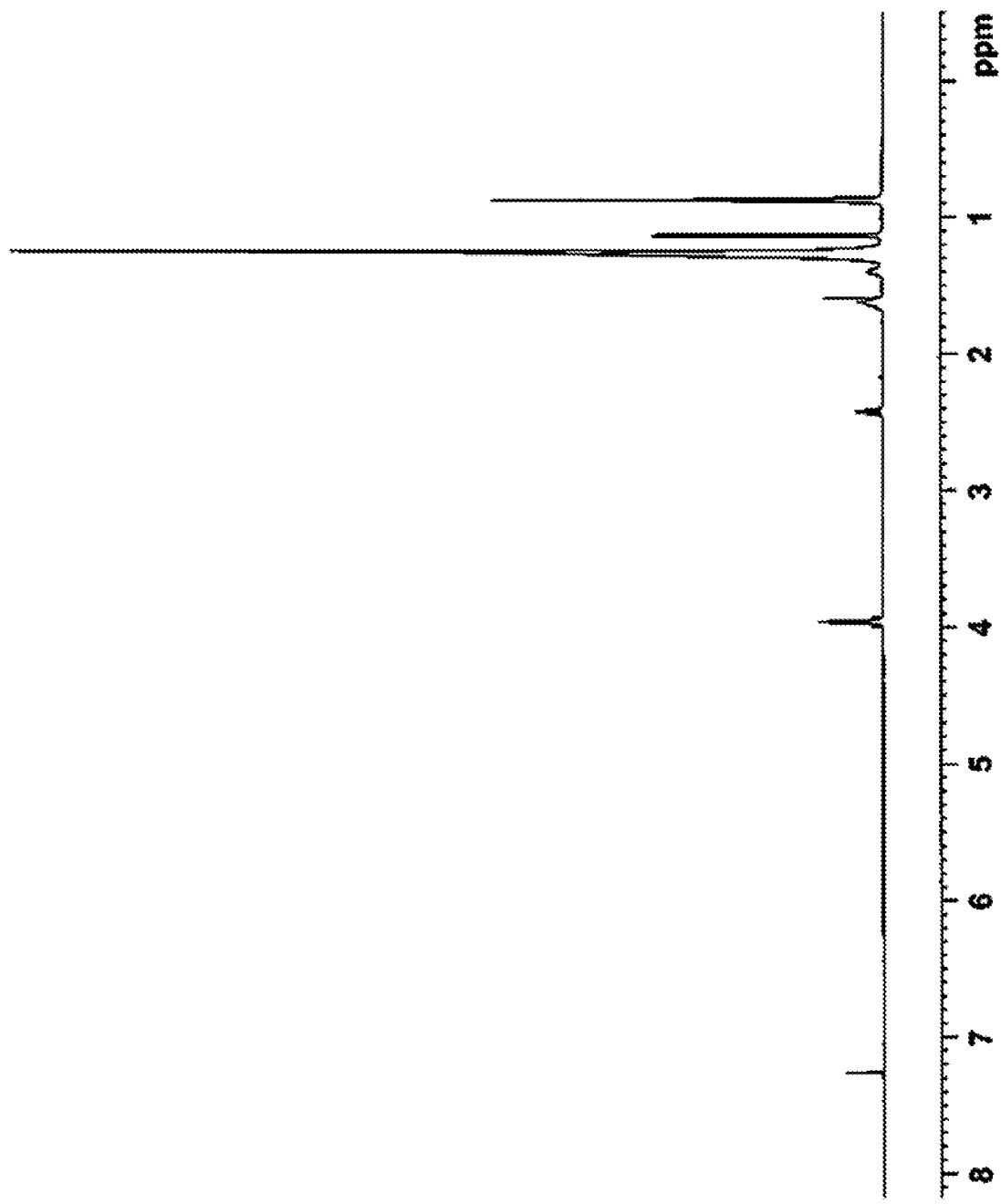
FIG. 14 illustrates a 1H-NMR spectrum of 2-octyldodecyl 2-methyloctanoate obtained in Example 7.

An IR spectrum and a 1H-NMR spectrum of 2-octyldodecyl 2-methyloctanoate were measured, and FIGS. 13 and 14 illustrate the spectra. In the $^1$H-NMR spectrum, the singlet peak around 7.26 ppm is derived from deuterated chloroform (solvent), and the singlet peak around 1.59 ppm is derived from water contained in the deuterated chloroform (solvent).

IR (cm$^{-1}$): 2956, 2922, 2854, 1735, 1464, 1378, 1246, 1168, 1146, 1087, 1038, 722

$^1$H-NMR (500 MHz, ppm): 0.86-0.89 (m, 9H), 1.13-1.14 (d, 3H), 1.26-1.28 (m, 40H), 1.37-1.44 (m, 1H), 1.61-1.67 (m, 2H), 2.39-2.46 (m, 1H), 3.93-4.00 (m, 2H)

Example 8

2-Octyldodecyl 2-methylnonanoate with an acid value of 0.01 KOH/g or less was obtained in the same manner as in Example 1 except that 2-methylnonanoic acid was used instead of 2-methylpentanoic acid, and that 2-octyldodecanol was used instead of 2-decyltetradecanol. The obtained 2-octyldodecyl 2-methylnonanoate ("ester (H)") was evaluated as a lubricating base oil for a fluid bearing. Table 1 illustrates the results.

Figure 15:
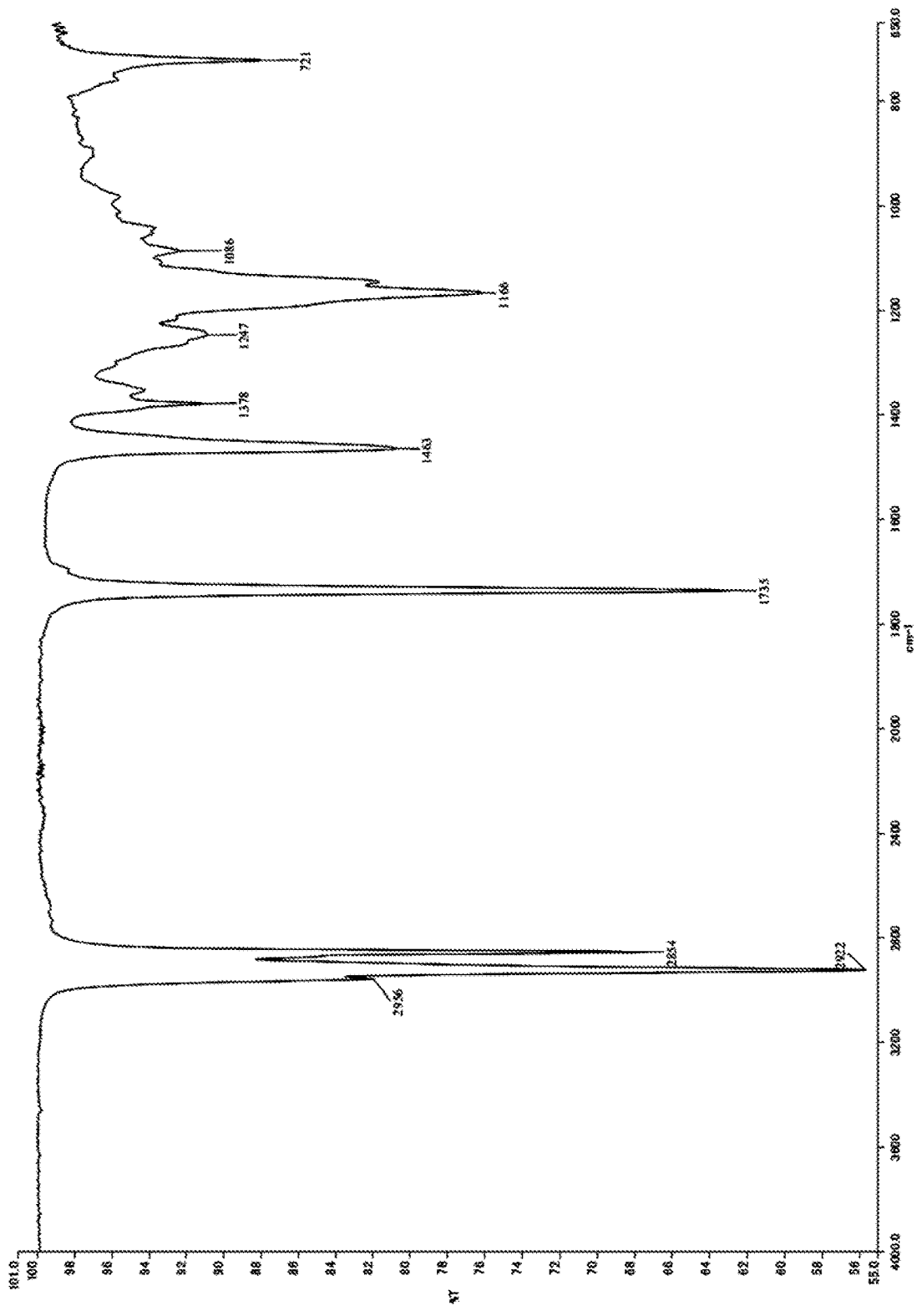
FIG. 15 illustrates an IR spectrum of 2-octyldodecyl 2-methylnonanoate obtained in Example 8.
Figure 16:
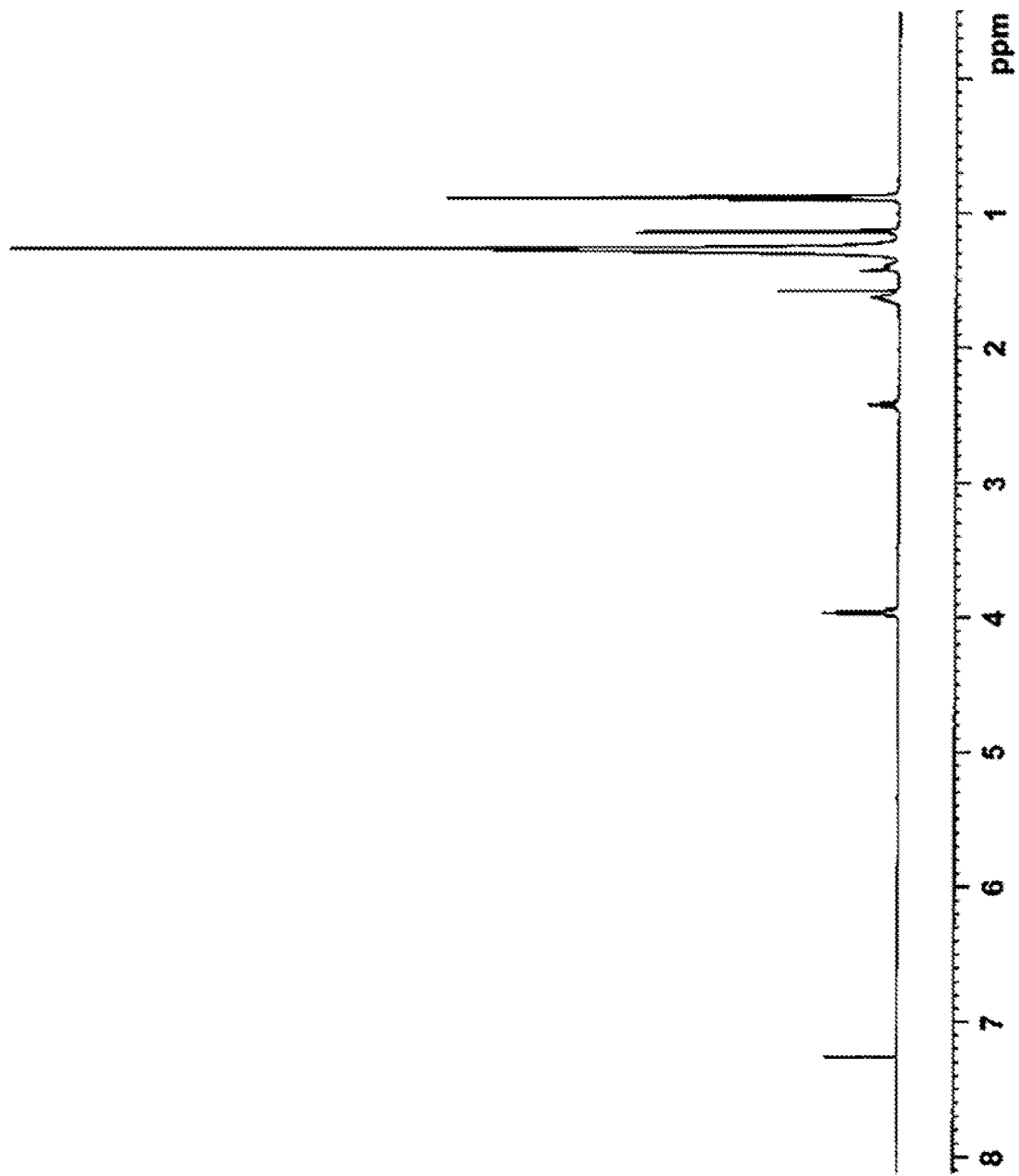
FIG. 16 illustrates a 1H-NMR spectrum of 2-octyldodecyl 2-methylnonanoate obtained in Example 8.

An IR spectrum and a 1H-NMR spectrum of 2-octyldodecyl 2-methylnonanoate were measured. FIGS. 15 and 16 illustrate the spectra. In the $^1$H-NMR spectrum, the singlet peak around 7.26 ppm is derived from deuterated chloroform (solvent), and the singlet peak around 1.58 ppm is derived from water contained in the deuterated chloroform (solvent).

IR (cm$^{-1}$): 2956, 2922, 2854, 1735, 1463, 1378, 1247, 1166, 1086, 721

$^1$H-NMR (500 MHz, ppm): 0.86-0.89 (m, 9H), 1.13-1.14 (d, 3H), 1.26 (m, 42H), 1.38-1.43 (m, 1H), 1.62-1.67 (m, 2H), 2.39-2.45 (m, 1H), 3.93-4.00 (m, 2H)

Example 9

A mixture of 2-pentylhexadecyl 2-methylheptanoate and 2-heptyltetradecyl 2-methylheptanoate with an acid value of 0.01 KOH/g or less (50:50) was obtained in the same manner as in Example 1 except that 2-methylheptanoic acid was used instead of 2-methylpentanoic acid, and that a mixture of 2-pentylhexadecanol and 2-heptyltetradecanol was used instead of 2-decyltetradecanol (50:50). The obtained mixture of 2-pentylhexadecyl 2-methylheptanoate and 2-heptyltetradecyl 2-methylheptanoate (50:50, molar ratio) ("ester (I)") was then evaluated as a lubricating base oil for a fluid bearing. Table 1 illustrates the results.

Figure 17:
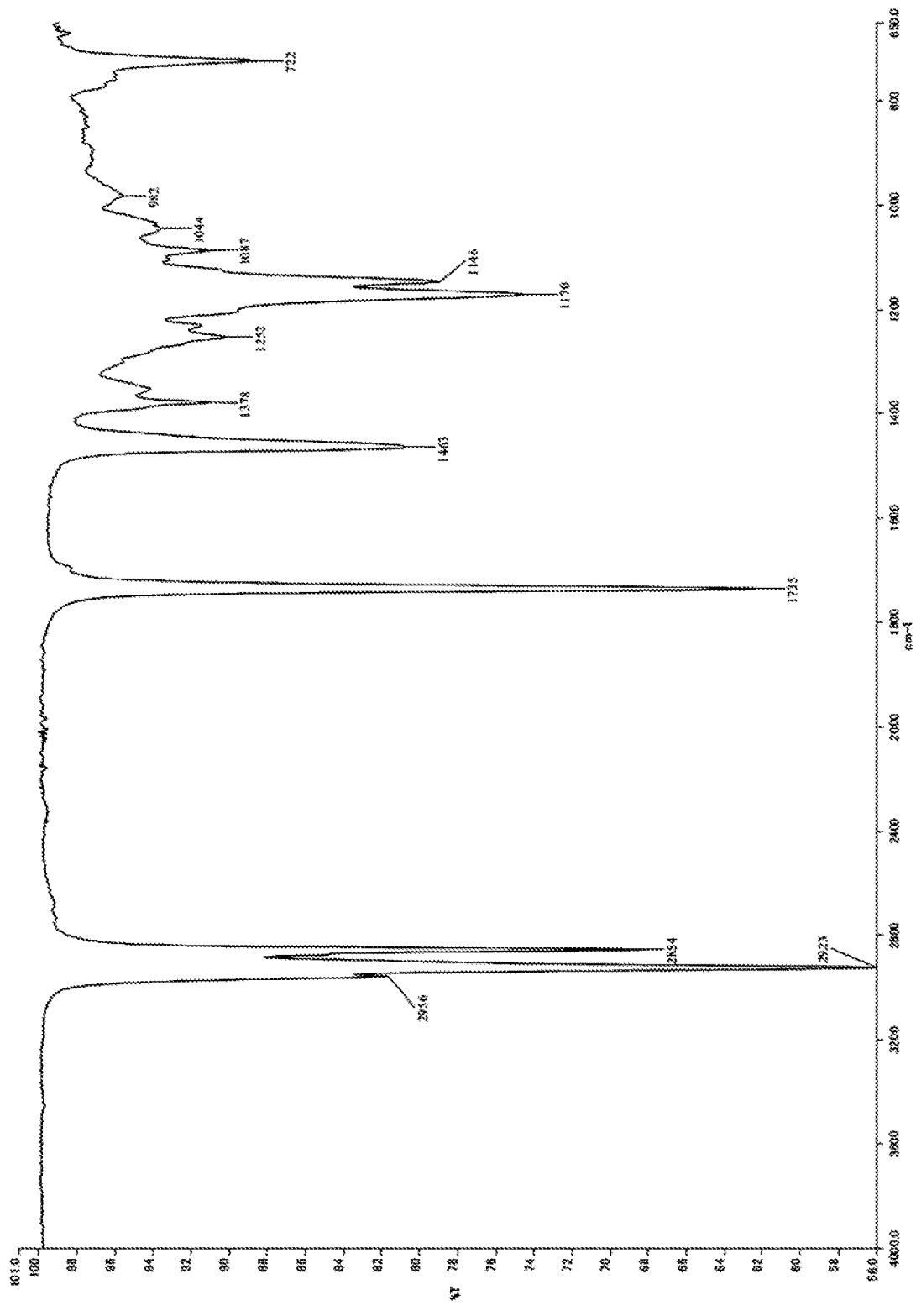
FIG. 17 illustrates an IR spectrum of a mixture of 2-pentylhexadecyl 2-methylheptanoate and 2-heptyltetradecyl 2-methylheptanoate (50:50) obtained in Example 9.

An IR spectrum of the mixture of 2-pentylhexadecyl 2-methylheptanoate and 2-heptyltetradecyl 2-methylheptanoate (50:50) was measured. FIG. 17 illustrates the spectrum.

IR (cm$^{-1}$): 2956, 2923, 2854, 1735, 1463, 1378, 1252, 1170, 1146, 1087, 1044, 982, 722

TABLE 1

| | Lubricating Base Oil for Fluid Bearing | Kinematic Viscosity [mm2/s] | | Viscosity Index (Evaluation) | Evaporation Resistance Weight Loss by 5% [° C.] (Evaluation) | Acid Value | | | Melting Point [° C.] (Evaluation) |
| --- | --- | --- | --- | --- | --- | --- | --- | --- | --- |
| | | 40° C. (Evaluation) | 100° C. | | | Initial Value [mg KOH/g] | After Hydrolysis Test [mg KOH/g] | Increase in Value [mg KOH/g] (Evaluation) | |
| Example 1 | Ester (A) | 12.7 (I) | 3.39 | 147 (I) | 270 (I) | ≤0.01 | 0.09 | 0.08 (I) | ≤20.6 (I) |
| Example 2 | Ester (B) | 14.4 (II) | 3.69 | 150 (I) | 279 (I) | ≤0.01 | 0.09 | 0.08 (I) | ≤11.5 (I) |

TABLE 1-continued

| | Lubricating Base Oil for Fluid Bearing | Kinematic Viscosity [mm2/s] 40° C. (Evaluation) | 100° C. | Viscosity Index (Evaluation) | Evaporation Resistance Weight Loss by 5% [° C.] (Evaluation) | Acid Value Initial Value [mg KOH/g] | After Hydrolysis Test [mg KOH/g] | Increase in Value [mg KOH/g] (Evaluation) | Melting Point [° C.] (Evaluation) |
|---|---|---|---|---|---|---|---|---|---|
| Example 3 | Ester (C) | 15.4 (II) | 3.87 | 152 (I) | 282 (I) | ≤0.01 | 0.08 | 0.07 (I) | ≤10.1 (I) |
| Example 4 | Ester (D) | 14.1 (II) | 3.59 | 144 (I) | 278 (I) | ≤0.01 | 0.07 | 0.06 (I) | ≤38.2 (I) |
| Example 5 | Ester (E) | 16.3 (II) | 4.05 | 155 (I) | 284 (I) | ≤0.01 | 0.08 | 0.07 (I) | ≤11.3 (I) |
| Example 6 | Ester (F) | 12.6 (I) | 3.53 | 145 (I) | 265 (I) | ≤0.01 | 0.08 | 0.07 (I) | ≤17.6 (I) |
| Example 7 | Ester (G) | 11.1 (I) | 3.01 | 131 (II) | 260 (I) | ≤0.01 | 0.08 | 0.07 (I) | ≤24.5 (I) |
| Example 8 | Ester (H) | 12.0 (I) | 3.19 | 134 (II) | 265 (I) | ≤0.01 | 0.07 | 0.06 (I) | ≤19.8 (I) |
| Example 9 | Ester (I) | 11.7 (I) | 3.14 | 136 (II) | 260 (I) | ≤0.01 | 0.07 | 0.06 (I) | −11.8 (I) |

Comparative Examples 1 to 12

As Comparative Examples, the following were evaluated as lubricating base oils for a fluid bearing: di(2-ethylhexyl) sebacate (DOS), an ester compound of n-decanoic acid and trimethylol propane (ester (a)), an ester compound of n-dodecanoic acid and 2-octyldodecanol (ester (b)), 2-hexyldecyl n-hexyldecanoate (ester (c)), n-undecyl 2-octyldodecanoate (ester (d)), an ester compound of 2-octyldodecanoic acid and 3,7-dimethyloctanol (ester (e)), n-nonyl 2-decyltetradecanoate (ester (f)), 2-hexyldecyl 2-butyltetradecanoate (ester (g)), 2-decyltetradecyl 2-ethylhexanoate (ester (h)), 2-octyldodecyl 2-ethylhexanoate (ester (i)), 2-decyltetradecyl n-octanoate (ester (j)), and n-hexadecyl 2-methylhexadecanoate (ester (k)). Table 2 illustrates the results.

TABLE 2

| | Lubricating Base Oil for Fluid Bearing | Kinematic Viscosity [mm2/s] 40° C. (Evaluation) | 100° C. | Viscosity Index (Evaluation) | Evaporation Resistance Weight Loss by 5% [° C.] (Evaluation) | Acid Value Initial Value [mg KOH/g] | After Hydrolysis Test [mg KOH/g] | Increase in Value [mg KOH/g] (Evaluation) | Melting Point [° C.] (Evaluation) |
|---|---|---|---|---|---|---|---|---|---|
| Comparative Example 1 | DOS | 11.5 (I) | 3.21 | 153 (I) | 262 (I) | ≤0.01 | 1.15 | 1.14 (III) | ≤−50.0 (I) |
| Comparative Example 2 | Ester (a) | 17.0 (III) | 3.94 | 130 (II) | 286 (I) | ≤0.01 | 10.78 | 10.77 (III) | −23.8 (I) |
| Comparative Example 3 | Ester (b) | 14.6 (II) | 3.79 | 158 (I) | 286 (I) | ≤0.01 | 0.27 | 0.26 (II) | 4.6 (III) |
| Comparative Example 4 | Ester (c) | 15.9 (II) | 4.06 | 164 (I) | 288 (I) | ≤0.01 | 0.28 | 0.27 (II) | 1.9 (III) |
| Comparative Example 5 | Ester (d) | 13.7 (I) | 3.56 | 148 (I) | 276 (I) | ≤0.01 | 0.08 | 0.07 (I) | 10.3 (III) |
| Comparative Example 6 | Ester (e) | 13.5 (I) | 3.36 | 125 (III) | 259 (II) | ≤0.01 | 0.08 | 0.07 (I) | −11.7 (I) |
| Comparative Example 7 | Ester (f) | 15.9 (II) | 3.97 | 154 (I) | 292 (I) | ≤0.01 | 0.08 | 0.07 (I) | 15.5 (III) |
| Comparative Example 8 | Ester (g) | 17.9 (III) | 4.01 | 123 (III) | 284 (I) | ≤0.01 | 0.03 | 0.02 (I) | −48.7 (I) |
| Comparative Example 9 | Ester (h) | 15.3 (II) | 3.75 | 138 (II) | 274 (I) | ≤0.01 | 0.08 | 0.07 (I) | −12.8 (I) |
| Comparative Example 10 | Ester (i) | 11.0 (I) | 2.91 | 115 (III) | 250 (II) | ≤0.01 | 0.07 | 0.06 (I) | ≤−50.0 (I) |
| Comparative Example 11 | Ester (j) | 14.6 (II) | 3.79 | 159 (I) | 290 (I) | ≤0.01 | 0.08 | 0.07 (I) | 1.3 (III) |
| Comparative Example 12 | Ester (k) | 17.5 (III) | 4.58 | 149 (I) | 299 (I) | ≤0.01 | 0.07 | 0.06 (I) | ≥20 (III) |

Examples 10 to 12

One part by mass of an antioxidant was added to 100 parts by mass of ester (B) as a lubricating base oil for a fluid bearing to prepare a lubricating oil composition for a fluid bearing according to the present invention. The prepared lubricating oil compositions for a fluid bearing were individually evaluated. Table 3 illustrates the results.

Examples 13 to 15

One part by mass of an antioxidant was added to 100 parts by mass of ester (C) as a lubricating base oil for a fluid bearing to prepare a lubricating oil composition for a fluid bearing according to the present invention. The prepared lubricating oil compositions for a fluid bearing were individually evaluated. Table 3 illustrates the results.

Examples 16 to 18

One part by mass of an antioxidant was added to 100 parts by mass of ester (H) as a lubricating base oil for a fluid bearing to prepare a lubricating oil composition for a fluid bearing according to the present invention. The prepared lubricating oil compositions for a fluid bearing were individually evaluated. Table 3 illustrates the results.

INDUSTRIAL APPLICABILITY

Due to its high viscosity index, and excellent evaporation resistance, hydrolytic stability, and low-temperature fluidity, the lubricating base oil for a fluid bearing according to the present invention is suitably used as a lubricating base oil for a fluid bearing.

The invention claimed is:

1. A lubricating base oil comprising a compound represented by general formula (1):

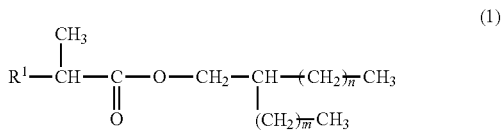

wherein $R^1$ represents a linear $C_2$-$C_{16}$ alkyl group, m represents an integer of 2 to 10, and n represents an integer of 4 to 14.

2. The lubricating base oil according to claim 1, having 27 to 35 carbon atoms in total.

3. The lubricating base oil according to claim 1, wherein the difference between n and m in general formula (1) is 2 to 9.

TABLE 3

| | Lubricating Base Oil [Parts by Mass] | Antioxidant [Parts by Mass] | Kinematic Viscosity [mm²/s] 40° C. (Evaluation) | 100° C. | Viscosity Index (Evaluation) | Evaporation Resistance Weight Loss by 5% [° C.] (Evaluation) | Acid Value Initial Value [mg KOH/g] | Acid Value After Hydrolysis Test [mg KOH/g] | Increase in Value [mg KOH/g] (Evaluation) | Melting Point [° C.] (Evaluation) |
|---|---|---|---|---|---|---|---|---|---|---|
| Exampe 10 | Ester (B) [100] | DODPA [1] | 14.7 (II) | 3.74 | 150 (I) | 279 (I) | <0.01 | 0.08 | 0.07 (I) | −11.5 (I) |
| Example 11 | Ester (B) [100] | MBDBP [1] | 14.8 (II) | 3.74 | 148 (I) | 279 (I) | <0.01 | 0.08 | 0.07 (I) | −11.5 (I) |
| Example 12 | Ester (B) [100] | DODPA [0.5] MBDBP [0.5] | 14.7 (II) | 3.73 | 148 (I) | 279 (I) | <0.01 | 0.08 | 0.07 (I) | −11.5 (I) |
| Example 13 | Ester (C) [100] | DODPA [1] | 15.7 (II) | 3.88 | 148 (I) | 282 (I) | <0.01 | 0.07 | 0.06 (I) | −10.2 (I) |
| Example 14 | Ester (C) [100] | MBDBP [1] | 15.8 (II) | 3.90 | 147 (I) | 282 (I) | <0.01 | 0.08 | 0.07 (I) | −10.1 (I) |
| Example 15 | Ester (C) [100] | DODPA [0.5] MBDBP [0.5] | 15.7 (II) | 3.88 | 148 (I) | 282 (I) | <0.01 | 0.08 | 0.07 (I) | −10.2 (I) |
| Example 16 | Ester (H) [100] | DODPA [1] | 12.3 (I) | 3.22 | 132 (II) | 265 (I) | <0.01 | 0.08 | 0.07 (I) | −19.8 (I) |
| Example 17 | Ester (H) [100] | MBDBP [1] | 12.4 (I) | 3.23 | 131 (II) | 265 (I) | <0.01 | 0.08 | 0.07 (I) | −19.7 (I) |
| Example 18 | Ester (H) [100] | DODPA [0.5] MBDBP [0.5] | 12.3 (I) | 3.22 | 132 (II) | 265 (I) | <0.01 | 0.07 | 0.06 (I) | −19.7 (I) |

Table 1 indicates that the lubricating base oil for a fluid bearing according to the present invention has a high viscosity index, and excellent evaporation resistance, hydrolytic stability, and low-temperature fluidity. Table 3 indicates that the lubricating oil composition for a fluid bearing according to the present invention also has a high viscosity index, and excellent evaporation resistance, hydrolytic stability, and low-temperature fluidity.

4. The lubricating base oil according to claim 1, wherein the content of the compound is 90 mass % or more based on the total mass of the lubricating base oil.

5. A lubricating oil composition comprising the lubricating base oil of claim 1.

6. The lubricating oil composition according to claim 5, further comprising an antioxidant.

* * * * *